US007579155B2

(12) United States Patent
Taylor et al.

(10) Patent No.: US 7,579,155 B2
(45) Date of Patent: Aug. 25, 2009

(54) METHOD FOR IDENTIFYING THE SEQUENCE OF ONE OR MORE VARIANT NUCLEOTIDES IN A NUCLEIC ACID MOLECULE

(75) Inventors: Paul D. Taylor, Gilroy, CA (US); Reyes Candau, Olney, MD (US); Gary F. Gerard, Frederick, MD (US)

(73) Assignee: Transgenomic, Inc., Omaha, NE (US)

( * ) Notice: Subject to any disclaimer, the term of this patent is extended or adjusted under 35 U.S.C. 154(b) by 0 days.

(21) Appl. No.: 12/101,255

(22) Filed: Apr. 11, 2008

(65) Prior Publication Data

US 2009/0068659 A1 Mar. 12, 2009

Related U.S. Application Data

(63) Continuation-in-part of application No. 11/854,181, filed on Sep. 12, 2007.

(51) Int. Cl.
*C12Q 1/68* (2006.01)
*C12P 19/34* (2006.01)
*C07H 21/00* (2006.01)
*C07H 21/02* (2006.01)
*C07H 21/04* (2006.01)

(52) U.S. Cl. ......................... 435/6; 435/91.2; 536/22.1; 536/23.1; 536/24.3

(58) Field of Classification Search ..................... 435/6, 435/440; 536/23.1, 24.3
See application file for complete search history.

(56) References Cited

U.S. PATENT DOCUMENTS 5,759,822 A * 6/1998 Chenchik et al. ........... 435/91.2
5,824,471 A * 10/1998 Mashal et al. .................. 435/6
5,830,721 A * 11/1998 Stemmer et al. .............. 506/10
5,851,770 A 12/1998 Babon et al.
5,869,245 A * 2/1999 Yeung ........................... 435/6
6,391,557 B1 * 5/2002 Yeung ........................... 435/6
6,699,980 B1 * 3/2004 Yeung ........................ 536/23.1
7,247,428 B2 * 7/2007 Makrigiorgos ................. 435/6
2003/0022215 A1 * 1/2003 Makrigiorgos ................. 435/6
2004/0166510 A1 * 8/2004 Gerard et al. .................. 435/6
2004/0209299 A1 * 10/2004 Pinter et al. .................... 435/6
2008/0274466 A1 * 11/2008 McKernan ..................... 435/6

FOREIGN PATENT DOCUMENTS

WO 02086169 A1 10/2002
WO WO 2006/053259 * 5/2006

OTHER PUBLICATIONS

Yang et al. Purification, Cloning, and Characterization of the CEL I Nuclease Biochemistry 39 : 3533-3541 (2000).*

Greene et al., Spectrum of Chemically induced mutations from a large-scale reverse-genetics screen in Arabidopis. Genetics 164 : 731-740 (Jun. 2003).*

Oleykowski et al., Mutation detection using a novel plant endonuclease. Nucleic Acids Research 26(20) : 4597-4602 (1998).*

Kulinski et al., CEL I enzymatic mutation detection assay. Biotechniques 29(1) : 44, 46 and 48 (2000).*

Chang et al., Base mismatch-specific endonuclease activity in extracts from Saccharomyces cerevisiae. Nucleic Acids Research 19 (17) : 4761-4766 (1991).*

Till et al., Large-scale discovery of induced point mutations with high-throughput TILLING. Genome Research 13 : 524-530 (2003).*

Colbert et al., High-throughput screening for induced point mutations. Plant Physiology 126 : 480-484 (2001).*

Hsu et al., Detection of DNA point mutations with DNA mismatch repair enzymes. Carcinogenesis 15(8) : 1657-1662 (1994).*

Slade et al., A reverse genetic, nontransgenic approach to wheat crop improvement by TILLING. Nature Biotechnology 23(1) : 75-81 (Jan. 2005).*

Qiu et al., Mutation detection using Surveyor nuclease. Biotechniques 36(4) : 702-7 (2004).*

Sokurenko et al. Detection of simple mutations and polymorphisms in large genomic regions. Nucleic Acids Research 29(22) e111 (2001).*

Qiu et al. A method for clone specific confirmation using a mismatch-specific DNA endonuclease. Molecular Biotechnology 29 : 11-18 (2005).*

Margulies et al., "Genome sequencing in microfabricated high-density picolitre reactors", Nature 2005 437(15):376-380.

Rao et al., "Establishing a method to detect the DNA damage of N-ras gene", J. Sichuan Univ. (Med. Sci. Edi.) 2005 36:779-791—Abstract.

Robertson et al., "Genome-wide profiles of STAT1 DNA association using chromatin immunoprecipitation and massively parallel sequencing", Nature Methods 2007 4(8):651-657.

Takatsu et al., "FRET-based analysis of SNPs without fluorescent probes", Nucleic Acids Research 2004 32:el156 (19):1-7.

Wu et al., :Study of rat's p53 gene damage and organ specifically induced by benzidine, J. Sichuan Univ. (Med. Sci. Edi.) 2006 37:33-34—Abstract.

Zhang et al., "Randomized Terminal Linker-dependent PCRA: A Versatile and Sensitive Method for Detection of DNA Damage", Biomedical and Environmental Sciences 2002 15:203-208.

* cited by examiner

*Primary Examiner*—Ethan Whisenant
(74) *Attorney, Agent, or Firm*—Licata & Tyrrell P.C.

(57) ABSTRACT

The invention relates to methods for identifying the sequence of one or more variant nucleotides in nucleic acid molecules. The method involves cleaving a double-stranded nucleic acid molecule containing a mismatch with a mismatch-specific endonuclease which cleaves on the 3' side of the mismatch, and preserving the integrity of the variant nucleotide by ligating a Double-Stranded Linker with a degenerate 3'-overhang to said variant nucleotide. Because the variant nucleotide is immediately adjacent to the linker, PCR and/or sequence-by-synthesis analysis can be readily carried out.

15 Claims, 6 Drawing Sheets

(SEQ ID NO:23)
CTCGACTGGAGCACGAGGACACTACTGGCC
440 450 460 470 480 490 500
TAGTTGGTTGCAAGATGTTGAATCCTGGAAGGAATCTCGACTGGAGCACGAGGACACTACTGGCC
(SEQ ID NO:24)

MISMATCH
LINKER

*FIG. 5A*

(SEQ ID NO:25)
CCGACTGGAGCACGAGGACACTACTGGCCGTC
170 180 190 200 210 220 230
TTAGATACTTATTGGCGCTAGTAGAGATATCATCACCGACTGGAGCACGAGGACACTACTGGCCGTC
(SEQ ID NO:26)

MISMATCH
LINKER

*FIG. 5B*

```
                                                BLOCKER
                                                   |
5'-P-CGACTGGAGCAC-GAGGACACTACTGGCCGACGTTTTACACC-3'  (SEQ ID NO:27)
3'-NNGCTGACCTCGTG CTCCTGTGATGACCGGCTGCAAAATGTGG-5   (SEQ ID NO:29)
   |(SEQ ID NO:28) |                                |
BLOCKER            3'-OH                          BIOTIN
```

*FIG. 6*

SEQUENCE LISTING

```
<160> NUMBER OF SEQ ID NOS: 29

<210> SEQ ID NO 1
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1

tgtaaaacga cggccagt                                     18
```

-continued

<210> SEQ ID NO 2
<211> LENGTH: 21
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(3)
<223> OTHER INFORMATION: "n" denotes any nucleotide

<400> SEQUENCE: 2
nnnacatttt gctgccggtc a 21

<210> SEQ ID NO 3
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 3
acacctgatc aagcctgttc atttgattac 30

<210> SEQ ID NO 4
<211> LENGTH: 30
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: Nucleotide labed with biotin

<400> SEQUENCE: 4
acacctgatc aagcctgttc atttgattac 30

<210> SEQ ID NO 5
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 5
ccaaagaatg atctgcggag cttcc 25

<210> SEQ ID NO 6
<211> LENGTH: 25
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: Nucleotide labeled with biotin

<400> SEQUENCE: 6
ccaaagaatg atctgcggag cttcc 25

<210> SEQ ID NO 7
<211> LENGTH: 41
<212> TYPE: DNA
<213> ORGANISM: Artificial sequence
<220> FEATURE:
<223> OTHER INFORMATION: Synthetic oligonucleotide

<400> SEQUENCE: 7
cgactggagc acgaggacac tactggccga cgttttacac c 41

<210> SEQ ID NO 8
<211> LENGTH: 44
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (42)..(44)
<223> OTHER INFORMATION: "n" denotes any nucleotide

<400> SEQUENCE: 8
ggtgtaaaac gacggccagt agtgtcctcg tgctccagtc gnnn 44

<210> SEQ ID NO 9
<211> LENGTH: 43
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (42)..(43)
<223> OTHER INFORMATION: "n" denotes any nucleotide

<400> SEQUENCE: 9
ggtgtaaaac gacggccagt agtgtcctcg tgctccagtc gnn 43

<210> SEQ ID NO 10
<211> LENGTH: 42
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (42)..(42)
<223> OTHER INFORMATION: "n" denotes any nucleotide

<400> SEQUENCE: 10
ggtgtaaaac gacggccagt agtgtcctcg tgctccagtc gn 42

<210> SEQ ID NO 11
<211> LENGTH: 32
<212> TYPE: DNA
<213> ORGANISM: Artificial sequence
<220> FEATURE:
<223> OTHER INFORMATION: Synthetic oligonucleotide

<400> SEQUENCE: 11
ggtgtaaaac gacggccagt agtgtcctcg tg 32

<210> SEQ ID NO 12
<211> LENGTH: 42
<212> TYPE: DNA
<213> ORGANISM: Artificial sequence
<220> FEATURE:
<223> OTHER INFORMATION: Synthetic oligonucleotide

<400> SEQUENCE: 12
ccatggtaag gatatgcact cccatggtaa ggatatgcac tc 42

<210> SEQ ID NO 13
<211> LENGTH: 22

-continued

```
<212> TYPE: DNA
<213> ORGANISM: Artificial sequence
<220> FEATURE:
<223> OTHER INFORMATION: Synthetic oligonucleotide

<400> SEQUENCE: 13

gagtttcgcc agattcaaca tc                                              22


<210> SEQ ID NO 14
<211> LENGTH: 48
<212> TYPE: DNA
<213> ORGANISM: Artificial sequence
<220> FEATURE:
<223> OTHER INFORMATION: Synthetic DNA
<220> FEATURE:
<221> NAME/KEY: misc_feature
<222> LOCATION: (1)..(1)
<223> OTHER INFORMATION: Nucleotide labeled with biotin

<400> SEQUENCE: 14

cacacatcca tcatcatcat gaattccaga catcaggcag gcatcaga                  48


<210> SEQ ID NO 15
<211> LENGTH: 48
<212> TYPE: DNA
<213> ORGANISM: Artificial sequence
<220> FEATURE:
<223> OTHER INFORMATION: Synthetic DNA

<400> SEQUENCE: 15

tctgatgcct gcctgatgtc tggaattcat gatgatgatg gatgtgtg                  48


<210> SEQ ID NO 16
<211> LENGTH: 41
<212> TYPE: DNA
<213> ORGANISM: Artificial sequence
<220> FEATURE:
<223> OTHER INFORMATION: Synthetic DNA

<400> SEQUENCE: 16

cgactggagc acgaggacac tactggccga cgttttacac c                         41


<210> SEQ ID NO 17
<211> LENGTH: 29
<212> TYPE: DNA
<213> ORGANISM: Artificial sequence
<220> FEATURE:
<223> OTHER INFORMATION: Synthetic DNA
<220> FEATURE:
<221> NAME/KEY: misc_feature
<222> LOCATION: (1)..(1)
<223> OTHER INFORMATION: Nucleotide labeled with biotin

<400> SEQUENCE: 17

ggtgtaaaac gtcggccagt agtgtcctc                                       29


<210> SEQ ID NO 18
<211> LENGTH: 14
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (13)..(14)
<223> OTHER INFORMATION: “n” denotes any nucleotide

<400> SEQUENCE: 18
```

-continued gtgctccagt cgnn 14

<210> SEQ ID NO 19
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 19
gcaaggaaat gagaacccag agagggcaag 30

<210> SEQ ID NO 20
<211> LENGTH: 27
<212> TYPE: DNA
<213> ORGANISM: Artificial sequence
<220> FEATURE:
<223> OTHER INFORMATION: Synthetic oligonucleotide

<400> SEQUENCE: 20
gatagactgc ctgtgggatc tagcctc 27

<210> SEQ ID NO 21
<211> LENGTH: 37
<212> TYPE: DNA
<213> ORGANISM: Artificial sequence
<220> FEATURE:
<223> OTHER INFORMATION: Synthetic oligonucleotide

<400> SEQUENCE: 21
ggtttaaacg aattccagac atcaggcagg catcaga 37

<210> SEQ ID NO 22
<211> LENGTH: 39
<212> TYPE: DNA
<213> ORGANISM: Artificial sequence
<220> FEATURE:
<223> OTHER INFORMATION: Synthetic oligonucleotide

<400> SEQUENCE: 22
ttgaatttag cggccggtgt aaaacgtcgg ccagtagtg 39

<210> SEQ ID NO 23
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 23
ctcgactgga gcacgaggac actactggcc 30

<210> SEQ ID NO 24
<211> LENGTH: 65
<212> TYPE: DNA
<213> ORGANISM: Artificial sequence
<220> FEATURE:
<223> OTHER INFORMATION: Synthetic oligonucleotide

<400> SEQUENCE: 24
tagttggttg caagatgttg aatcctggaa ggaatctcga ctggagcacg aggacactac 60
tggcc 65

<210> SEQ ID NO 25
<211> LENGTH: 32

-continued

```
<212> TYPE: DNA
<213> ORGANISM: Artificial sequence
<220> FEATURE:
<223> OTHER INFORMATION: Synthetic oligonucleotide

<400> SEQUENCE: 25

ccgactggag cacgaggaca ctactggccg tc                                    32


<210> SEQ ID NO 26
<211> LENGTH: 67
<212> TYPE: DNA
<213> ORGANISM: Artificial sequence
<220> FEATURE:
<223> OTHER INFORMATION: Synthetic oligonucleotide

<400> SEQUENCE: 26

ttagatactt attggcgcta gtagagatat catcaccgac tggagcacga ggacactact      60

ggccgtc                                                                67


<210> SEQ ID NO 27
<211> LENGTH: 41
<212> TYPE: DNA
<213> ORGANISM: Artificial sequence
<220> FEATURE:
<223> OTHER INFORMATION: Synthetic oligonucleotide

<400> SEQUENCE: 27

cgactggagc acgaggacac tactggccga cgttttacac c                          41


<210> SEQ ID NO 28
<211> LENGTH: 14
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(2)
<223> OTHER INFORMATION: "n" denotes any nucleotide

<400> SEQUENCE: 28

nngctgacct cgtg                                                        14


<210> SEQ ID NO 29
<211> LENGTH: 29
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (29)..(29)
<223> OTHER INFORMATION: Nucleotide labeled with biotin

<400> SEQUENCE: 29

ctcctgtgat gaccggctgc aaaatgtgg                                        29
```

METHOD FOR IDENTIFYING THE SEQUENCE OF ONE OR MORE VARIANT NUCLEOTIDES IN A NUCLEIC ACID MOLECULE

INTRODUCTION

This application is a continuation-in-part of U.S. Ser. No. 11/854,181 filed Sep. 12, 2007, which is herein incorporated by reference in its entirety.

BACKGROUND OF THE INVENTION

Identifying genome sequence variations between individuals is valued because it has the potential to explain phenotypes, disease predisposition, response to disease treatments and mechanisms of disease which may lead to more effective drug development. Sequencing the whole genomes of individuals is still an expensive and time consuming procedure although recent technologies based on sequencing-by-synthesis have made great progress. More economical, efficient and error-free methods of identifying sequence variation are needed.

The activity of mismatch-specific endonucleases has found utility in detection of sequence variations in otherwise identical DNA strands. A heteroduplex must first be produced between one reference DNA strand and the complement of the sample strand. If the sequences are exactly complementary with no mismatched bases, no cleavage takes place. If, however, they are not exactly complementary and mismatched bases are present, cleavage takes place with high specificity at the sites of mismatch. The cleaved products are conventionally detected by separation technologies based on fragment size. Thus, not only is the presence of mismatches revealed, the approximate location of the mismatch can also be inferred. For final identification of the exact nature of the difference between the sequences, Sanger sequencing is conventionally employed. Mismatch-specific endonuclease activity can therefore be used in an effective screening method capable of discriminating between samples which do and do not require additional sequence analysis. Such a screening process can reduce the numbers of samples that need to be fully sequenced saving both time, money and the processing, analysis & storage if excessive quantities if data.

CEL I and CEL II DNA endonucleases are examples of endonucleases which are known to cut double-stranded DNA in both strands at sites of single-base substitution, insertion or deletion. These enzymes cleave DNA on the 3'-side of the mismatch site, generating single-stranded 3'-overhangs of one or more nucleotides (Oleykowski, et al. (1998) *Nucleic Acids Res.* 26:4597-4602; Yang, et al. (2000) *Biochemistry* 39:3533-3541; Sokurenko, et al. (2001) *Nucleic Acids Res.* 29:e111; Qiu, et al. (2004) *BioTechniques* 37:702-707). These enzymes are routinely used to detect and map the location of unknown mutations in PCR-amplified DNA fragments (see, e.g., Kuliski, et al. (2000) *Biotechniques* 29:44-48; Colbert, et al. (2001) *Plant Physiol.* 126:480-484; Till, et al. (2003) *Genome Res.* 13:524-530; Greene, et al. (2003) *Genetics* 164:731-740; Slade, et al. (2005) *Nat. Biotechniques* 23:75-81). Detection and mapping involves PCR amplification of target DNA, annealing of the amplified DNA to form a mixture of homoduplices and heteroduplices, digestion with mismatch-specific endonuclease, and fractionation of the undigested homoduplices and heteroduplices from the digested products on a platform that separates DNA fragments based upon size. Endonuclease mutation detection and mapping, however, does not reveal the identity of a mutation, which requires DNA sequencing. Therefore, there is a need in the art to simplify mutation detection and concurrently determine the nature of the variation. The present invention meets this need in the art.

SUMMARY OF THE INVENTION

The present invention is a method for identifying the sequence of one or more variant nucleotides in a nucleic acid molecule. The method of the invention involves:

(a) contacting a double-stranded nucleic acid molecule with a mismatch-specific endonuclease, wherein one strand of said double-stranded nucleic acid molecule has one or more variant nucleotides which create at least one mismatch in the double-stranded nucleic acid molecule so that the double-stranded nucleic acid molecule is cleaved at the 3'-side of the mismatch by the mismatch-specific endonuclease;

(b) ligating a Double-Stranded Linker, containing a 3'-overhang, to the 3'-end of the strand with the one or more variant nucleotides, wherein the 3'-overhang of the linker is degenerate and the double-stranded portion of the linker is of a predetermined sequence; and (c) determining the sequence of the one or more variant nucleotides via the predetermined linker sequence thereby identifying the sequence of the one or more variant nucleotides.

In accordance with some embodiments, the 5'-end of at least one strand of the double-stranded nucleic acid molecule in step (a) is optionally bound to a solid support; the 3'-ends of the double-stranded nucleic acid molecule in (a) are blocked; the strand with the one or more variant nucleotides is labeled; the Double-Stranded Linker is detectably labeled; or the double-stranded nucleic acid molecule of step (a) is produced by a polymerase chain reaction, wherein the polymerase chain reaction is carried out with a universal primer and wherein the 5'-end of the universal primer is optionally bound to a solid support.

Some embodiments provide that the cleaved double-stranded nucleic acid molecule in (b) is denatured and the strand with the one or more variant nucleotides is isolated prior to ligation to the Double-Stranded Linker in step (b).

While particular embodiments provide that step (c) is carried out by sequencing-by-synthesis from the predetermined linker sequence, other embodiments provide that step (c) is carried out by: (i) denaturing the double-stranded portion of the linker; (ii) hybridizing a complementary primer to the predetermined linker sequence in the presence of an intercalating fluorescence resonance energy transfer (FRET) donor; (iii) contacting the product of step (ii) with DNA Polymerase and at least one ddNTP labeled with a FRET acceptor to extend the complementary primer; and (iv) detecting FRET, wherein the presence of FRET is indicative of the sequence of the variant nucleotide.

In other embodiments, the double-stranded nucleic acid molecule of step (a) is double-stranded genomic DNA produced by: (i) fragmenting one or more samples of genomic DNA; (ii) denaturing and annealing the fragmented genomic DNA to generate double-stranded genomic DNA molecules, wherein one strand of said double-stranded genomic DNA molecules has one or more variant nucleotides which create at least one mismatch in the double-stranded genomic DNA molecules; (iii) blunt ending, dephosphorylating 3' ends, and phosphorylating 5' ends of the double-stranded genomic DNA molecules; (iv) ligating a Double-Stranded Adaptor onto ends of the double-stranded genomic DNA molecules, wherein said Double-Stranded Adaptor contains a restriction enzyme cut site and a functional group at one 5' end; (v) size fractionating the double-stranded genomic DNA molecules of step (iv) removing un-ligated Double-Stranded Adaptor; (vi) immobilizing the size fractionated, double-stranded genomic DNA molecules via binding of the functional group of the Double-Stranded Adaptor to reactive groups of a first solid support; and (vii) removing double-stranded genomic DNA molecules which are not immobilized by the first solid support. In the context of the claimed method, this embodiment provides that the Double-Stranded Linker further includes a nick and a functional group at the 5' end of the strand containing the degenerate sequence and step (b) provides for: (i) immobilizing the Double-Stranded Linker ligated to the immobilized double-stranded genomic DNA molecules via binding of the functional group of the Double-Stranded Linker to reactive groups of a second solid support; and (ii) contacting the double-stranded genomic DNA molecules immobilized on the first solid support and second solid support with a restriction enzyme which cleaves the Double-Stranded Adaptor at the restriction enzyme cut site thereby releasing the double-stranded genomic DNA molecules from the first solid support.

The present invention is also a method for producing a library of genomic DNA molecules containing genetic variations. The method involves:

(a) fragmenting one or more samples of genomic DNA;

(b) denaturing and annealing the fragmented genomic DNA to generate double-stranded genomic DNA molecules, wherein one strand of said double-stranded genomic DNA molecules has one or more variant nucleotides which create at least one mismatch in the double-stranded genomic DNA molecules;

(c) blunt ending, dephosphorylating 3' ends, and phosphorylating 5' ends of the double-stranded genomic DNA molecules;

(d) ligating a Double-Stranded Adaptor onto ends of the double-stranded genomic DNA molecules, wherein said Double-Stranded Adaptor contains a restriction enzyme cut site and a functional group at one 5' end;

(e) size fractionating the double-stranded genomic DNA molecules of step (d) to remove un-ligated Double-Stranded Adaptor;

(f) immobilizing the size fractionated, double-stranded genomic DNA molecules via binding of the functional group of the Double-Stranded Adaptor to reactive groups of a first solid support;

(g) removing double-stranded genomic DNA molecules which are not immobilized at both ends by the first solid support;

(h) contacting the immobilized double-stranded genomic DNA molecules with a mismatch-specific endonuclease so that the double-stranded genomic DNA molecules are cleaved at the 3'-side of the mismatches therein;

(i) ligating a Double-Stranded Linker to the 3'-end of the immobilized genomic DNA molecules, wherein one strand of the Double-Stranded Linker has a nick, a functional group at the 5' end and a degenerate sequence at the 3' end, wherein the degenerate sequence is a 3' overhang, and the double-stranded portion of the linker is of a predetermined sequence;

(j) repairing the nicked DNA of the product of step (i);

(k) immobilizing the Double-Stranded Linker ligated to the immobilized double-stranded genomic DNA molecules via binding of the functional group of the Double-Stranded Linker to reactive groups of a second solid support; and (l) contacting the product of step (k) with a restriction enzyme which cleaves the Double-Stranded Adaptor at the restriction enzyme cut site thereby releasing the double-stranded genomic DNA molecules from the first solid support thereby creating a library of genomic DNA molecules containing genetic variations attached to the second solid support. In some embodiments of the invention, steps (h) through (k) are repeated one or more times.

A kit for identifying the sequence of one or more variants in a nucleic acid molecule is also provided by the present invention. Such a kit includes a mismatch-specific endonuclease that cleaves a double-stranded nucleic acid molecule at the 3'-side of a mismatch; and a Double-Stranded Linker, containing a 3'-overhang, wherein the 3'-overhang of the linker is degenerate and the double-stranded portion of the linker is of a predetermined sequence. In certain embodiments, the kit further includes a primer complementary to the predetermined sequence of the linker; an intercalating FRET donor; and ddCTP, ddATP, ddTTP and ddGTP each labeled with a different FRET acceptor. In yet other embodiments, the kit includes a Double-Stranded Adaptor containing a restriction site.

BRIEF DESCRIPTION OF THE DRAWINGS

FIG. 5 shows chromatograms of the nucleic acid sequences upstream (FIG. 5A) and downstream (FIG. 5B) of mismatches between a variant and reference sequence in Control G/C which was captured, amplified and sequenced. The nucleotides at the mismatch and the linker sequence are indicated. Mismatch, linker and linker sequence (including the mismatch) are shown.

FIG. 6 depicts the structure of an exemplary Double-Stranded Linker used in the production of a library of genomic DNA molecules containing genetic variations.

DETAILED DESCRIPTION OF THE INVENTION

Figure 1:
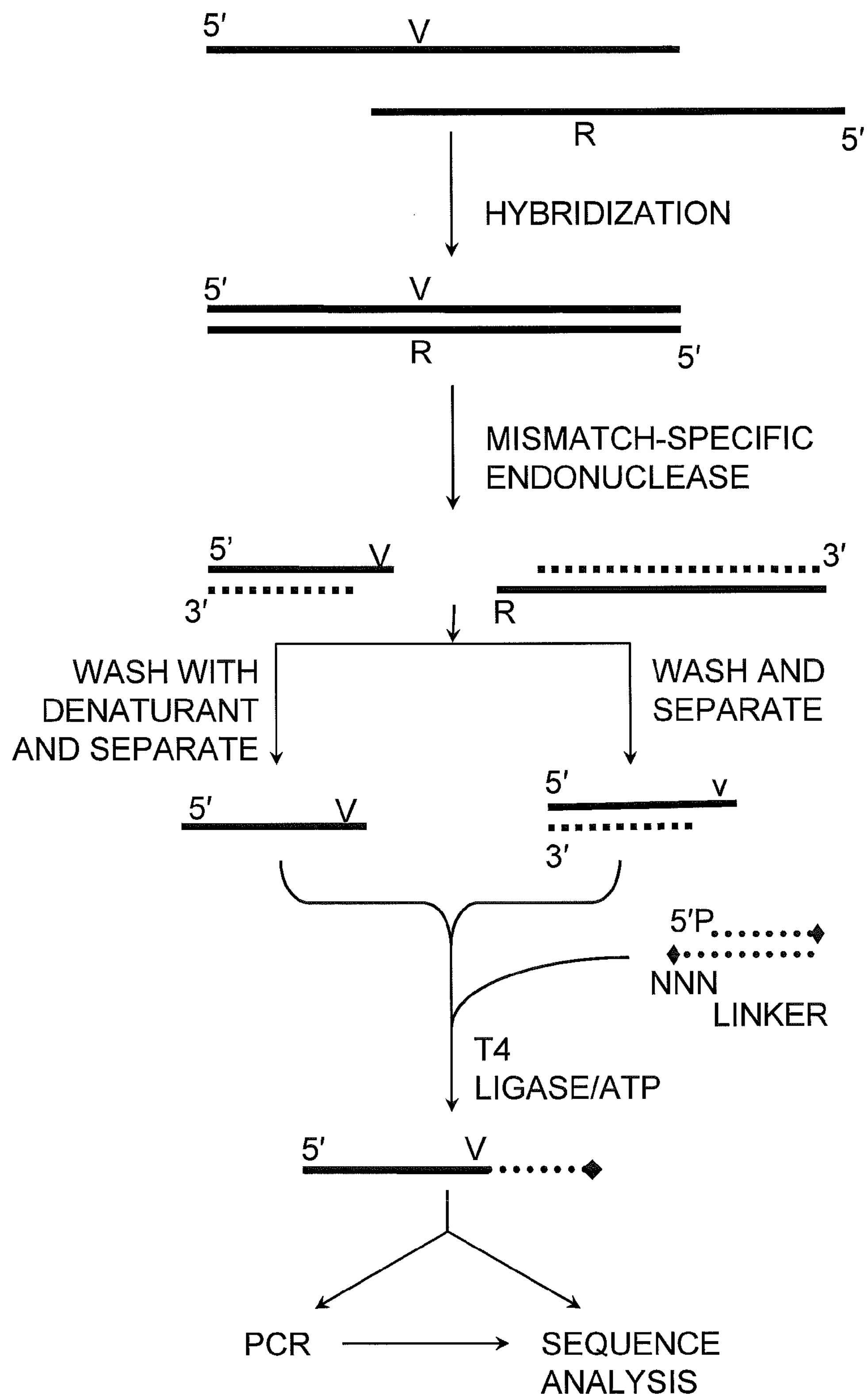
FIG. 1 shows a schematic of a method embraced by the present invention. The DNA strands represented by the solid-lines contain the nucleotides involved in the mismatch at their 3'-ends. The variant nucleotide is indicated by V, the reference nucleic acid with reference nucleotide R is also indicated. The degenerate Double-Stranded Linker is ligated to the 3'-end of the cleaved mismatch. In this instance three-base degeneracy is indicated by the bases NNN.

The present invention is the use of a randomized Double-Stranded Linker to capture a single, mismatch-specific endonuclease cleavage product along with its mismatch cut-site 3'-overhang with no a priori knowledge of the sequence at the 3'-mutation end. Advantageously, the instant method provides both the identification of the sequence of the variant nucleotide, as well as the context of the mutation. In this regard, the present invention provides a rapid method for the parallel detection and identification of variations in nucleic acid molecules. While it is contemplated that one or more variations can be readily detected and identified using the instant method, for simplicity and clarity, FIG. 1 depicts the method of the invention in the identification of a single nucleotide polymorphism or mutation. As shown in FIG. 1, a single-stranded sample nucleic acid molecule containing nucleotide variation (V) is hybridized with a single-stranded reference or wild-type nucleic acid molecule with reference nucleotide (R) to produce a double-stranded nucleic acid molecule with a mismatch. Upon contact of the double-stranded nucleic acid molecule with a mismatch-specific endonuclease, the double-stranded nucleic acid molecule is cleaved at the 3'-side of the mismatch. Because direct sequence analysis of the resulting molecule is confounded by the fact that the bases of most interest are at the very tip of the 3'-end, the instant method provides attaching a linker to the 3'-end of the cleaved variant nucleic molecule. To preserve the variant nucleotide at the 3'-end, the linker is double-stranded and contains a randomized or degenerate 3'-overhang to facilitate the efficiency of annealing to the variant single-stranded nucleic acid molecule. Advantageously, the double-stranded portion of the linker is of a pre-determined sequence (e.g., a universal sequence) thereby providing a site for a primer (e.g., a universal primer) to anneal for polymerase chain reaction (PCR) and/or sequence analysis of the variant nucleotide immediately adjacent to the linker sequence.

In accordance with the present method, the double-stranded or duplex nucleic acid molecule is formed by hybridizing a single-stranded sample or variant nucleic acid molecule (e.g., containing, or suspected of containing, a SNP or mutation) with a complementary or nearly complementary single-stranded reference molecule (e.g., a molecule with a known or wild-type sequence) such that any differences form a mismatch. The double-stranded molecule can be produced by restriction endonuclease cleavage or mechanical shearing of genomic or cDNA molecules, PCR amplification, or a combination thereof, followed by conventional mixing, denaturation and annealing.

In the preparation of the starting material, it is contemplated that adaptamers, which contain a 5'-end followed directly by a template-specific end, or linkers with specific 'sticky ends' (e.g., to anneal to restriction endonuclease sites) can be used to facilitate the direct PCR amplification of sample and reference nucleic acid molecules. Alternatively, sample and reference nucleic acid molecules can be amplified by conventional cloning techniques. When employing PCR, in particular in the amplification of a cloned DNA molecule or a DNA molecule with linker or adaptamer sequences attached thereto, certain embodiments of the present invention embrace the use of universal primers which anneal to vector, linker or adaptamer sequences. In this regard, universal primers, preferably with distinct sequences, are used to initially amplify the sample and reference nucleic acid molecules. Such universal primers and sequences are well-known in the art and include, but are not limited to M13(−20), T7 and the like.

Figure 2A:
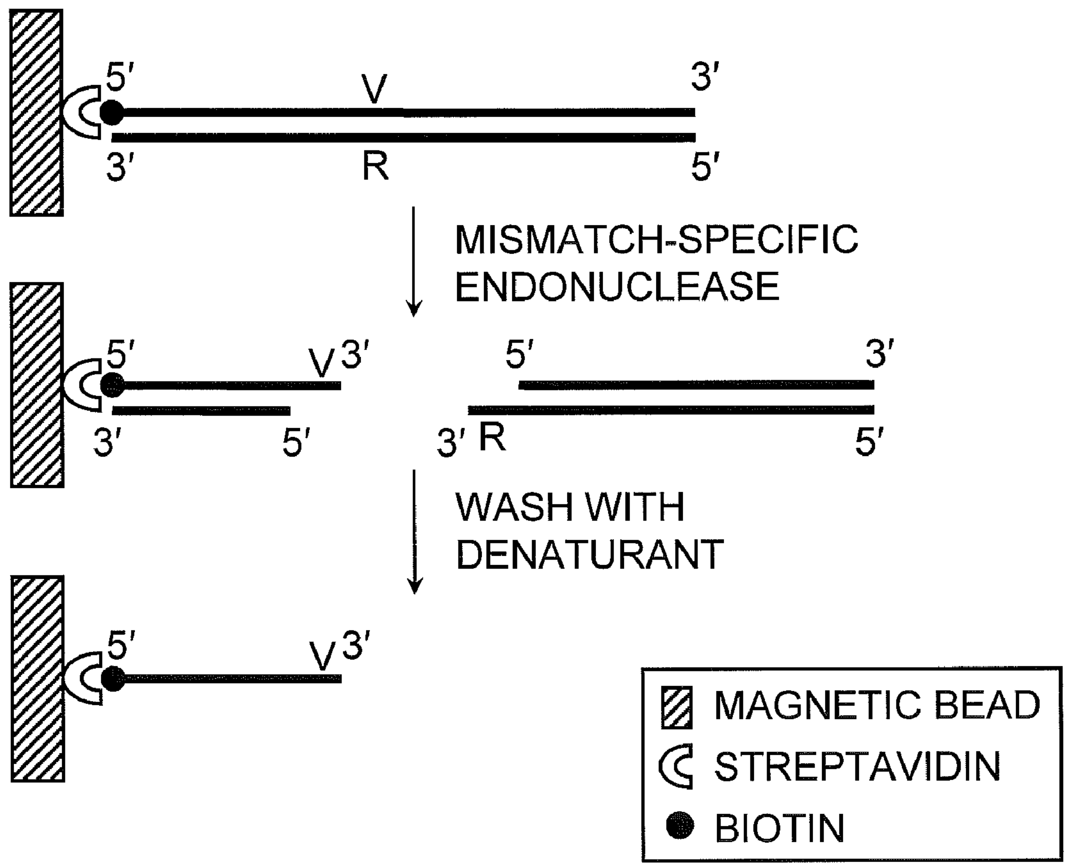
FIG. 2 depicts schematics of a method of the present invention, wherein either the variant nucleic acid molecule (FIG. 2A) or reference nucleic acid molecule (FIG. 2B) is attached to a solid support such as Streptavidin-coated magnetic beads via biotin. To prevent ligation of the Double-Stranded Linker to the reference non-cleaved nucleic acid molecule, the free 3'-OH groups can be capped prior to mismatch-specific endonuclease cleavage.

When it is desirable to isolate the single-stranded sample and/or reference nucleic acid molecules, some embodiments embrace immobilization of the single-stranded sample and/or reference nucleic acid molecules on a solid support. Immobilization on a solid support can be accomplished by attaching a functional group to the 5'-end of the nucleic acid molecule, wherein the functional group non-covalently interacts with a non-soluble entity such as a reactive group on a solid support such as a membrane, particle, bead or gel. For example, a hydrophobic group on the 5'-end of the nucleic acid molecule can be used to immobilize the nucleic acid molecule on a hydrophobic bead. Covalent attachment via thiol- or amino-derivatized nucleotides to a reactive group on a solid support is also embraced by the invention. By way of illustration, FIG. 2A depicts a biotinylated single-stranded sample nucleic acid molecule immobilized on a Streptavidin-coated, magnetic bead, wherein upon hybridization to a reference molecule and cleavage by a mismatch-specific endonuclease, the single-stranded sample nucleic acid molecule containing the variant nucleotide can be readily isolated. In this illustrative example, the biotin is the function group and Streptavidin is the reactive group on the solid support. Alternatively, it is contemplated that the reference molecule can be immobilized such that upon cleavage by a mismatch-specific endonuclease and subsequent denaturation, the double-stranded reference nucleic acid molecule can be removed, leaving the sample nucleic acid molecule free in solution. See FIG. 2B. In accordance with this embodiment, the 3'-end of reference molecule annealed to the sample nucleic acid molecule containing the variant nucleotide can be blocked or capped to prevent subsequent Double-Stranded Linker ligation.

The attachment of functional groups to nucleic acid molecules is routinely carried out in the art and any suitable method can be employed. However, in one embodiment, the functional group is attached to a universal primer used in the PCR amplification of the sample and/or reference nucleic acid molecule. Alternatively, other embodiments embrace ligating an adaptor to the nucleic acid molecule of interest, wherein the adaptor has a functional group attached thereto.

Hybridization of single-stranded sample and reference nucleic acid molecules can also be carried out using routine methods and conditions. Particular embodiments, however, embrace the use of quantitative strand exchange methods. An example of such a method is disclosed, e.g., by Arguello, et al. (1997) *Nucleic Acids Res.* 25:2236-2238). When two nearly identical sequences of double-stranded DNA are denatured and annealed, the yield of heteroduplex can be variable. Purely random annealing can lead to the highest yield $(x+y)\cdot(x+y)$, where x is the amount of one species and y is the amount of the second species. This gives the $xy+yx+x^2+y^2$ distribution of two heteroduplices (xy and yx) and two homoduplices ($x^2$ and $y^2$). If x=y then the 1:1:1:1 ratio is produced. However, this maximum yield is often not attained. For example, if the two sequences have a large number of mismatches, then the melting temperatures of the heteroduplices are much reduced compared to the homoduplices and they will not form at temperatures at which the homoduplices are almost fully annealed. Thus, stringent annealing of homoduplices can be virtually complete during cooling before heteroduplices have the chance to form.

As indicated supra, particular embodiments embrace capping or blocking pre-existing 3'-OH groups of nucleic acid molecules prior to mismatch-specific endonuclease cleavage so that Double-Stranded Linker ligation to these pre-existing 3'-OH groups is prevented. Any conventional capping or blocking group can be employed. For example, capping can be achieved by untemplated extension with a dideoxy base such as that produced by the enzyme terminal transferase together with a ddNTP. Capping with terminal transferase involves contacting the nucleic acid molecule of interest with any one of the ddNTPs in the presence of terminal transferase so that the enzyme adds a ddNTP to the 3'-OH, thereby preventing ligation to the 3'-OH group.

As an alternative to capping with terminal transferase, a capping adaptor can be employed, wherein said adaptor has a sequence which is different from the Double-Stranded Linker which is ligated to the mismatch-specific endonuclease cleavage product. To facilitate the synthesis of such a capping adaptor, it is contemplated that the capping adaptor can have a hairpin structure.

Subsequent to annealing, mismatches in the double-stranded nucleic acid molecule are recognized and cleaved by a mismatch-specific endonuclease. In accordance with this invention, the mismatch-specific endonucleases cleaves double-stranded nucleic acid molecules on the 3'-side of a mismatch. Exemplary mismatch-specific endonucleases of this type include, but are not limited to, CEL I and CEL II, and the like. Such enzymes are known in the art and commercially available from sources such as Transgenomic (Omaha, Nebr.).

Alternatively, a free 3'-OH can be generated at a mismatch by depolymerization and pyrophosphorylation as described in WO 02/086169 and U.S. Pat. No. 7,247,428, incorporated herein by reference. In this approach, a nucleic acid molecule of interest is depolymerized from the original intact 3'-OH end back to the mismatch site by pyrophosphosphorylation with a polymerase enzyme driven to catalyze the reverse of the normal polymerization by a large excess of pyrophosphate. The fact that mismatched bases are not a substrate of this pyrophosphorylation activity is exemplified by the PROMEGA READIT genotyping kit (see, Tsongalis, et al. (2001) *Exper. Mol. Pathol.* 71:222-225).

Figure 2B:
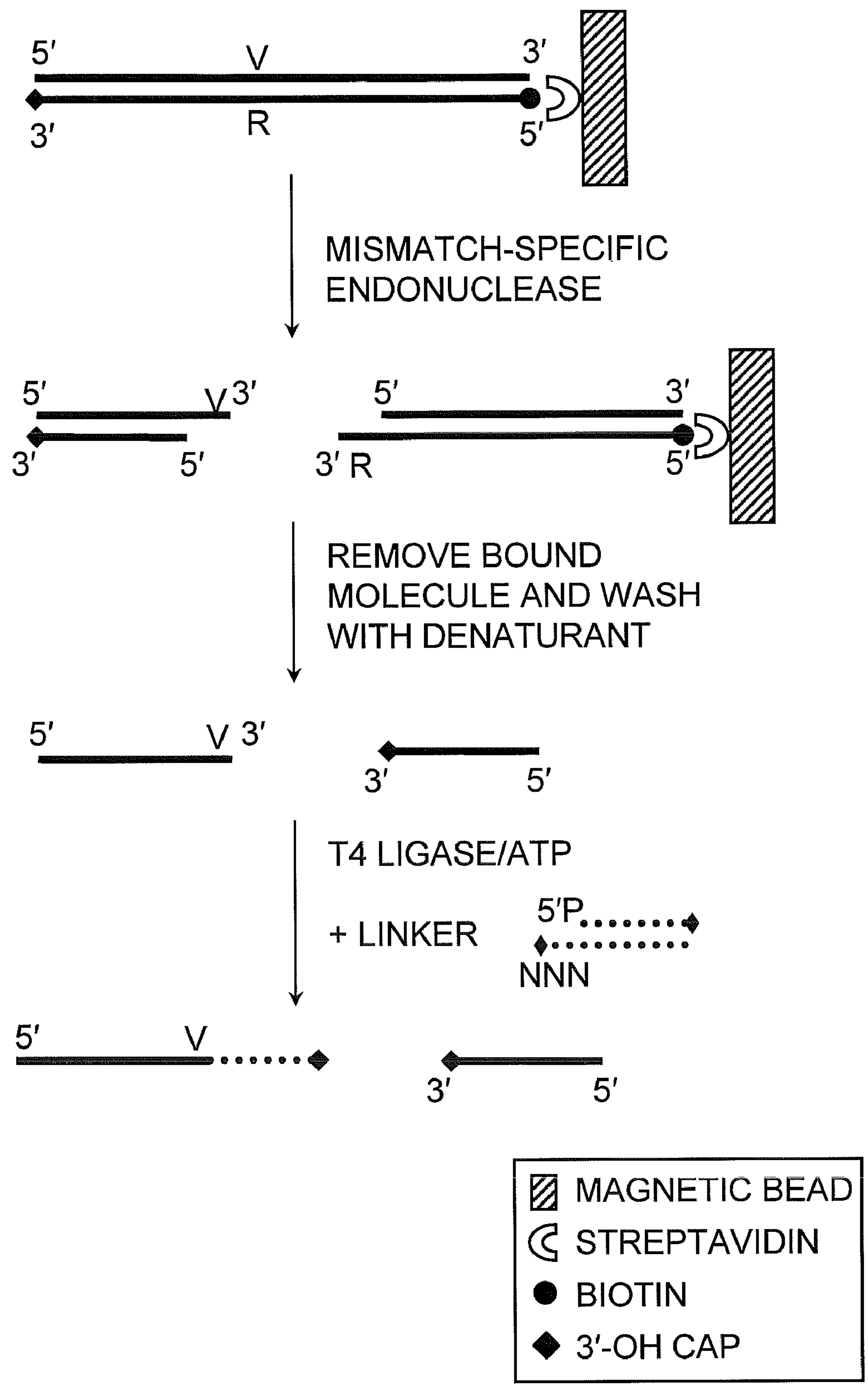

After cleaving the double-stranded nucleic acid molecule (i.e., the heteroduplex), the nucleic acid molecule containing one or more variant nucleotides, also referred to herein as the variant single-stranded nucleic acid molecule or sample nucleic acid molecule, can be directly ligated to the Double-Stranded Linker with or without being isolated from the other strand of the double-stranded nucleic acid molecule. As depicted in FIG. 1, isolation of the variant single-stranded nucleic acid molecule can involve washing with a denaturant to generate single-stranded molecules and separating the single-stranded molecules. Such separation can be carried out using conventional size separation procedures or alternatively by tagging the single-stranded molecules. By way of illustration, FIG. 2A shows that when the variant single-stranded nucleic acid molecule is bound to a solid support, denaturation and washing will remove the unwanted molecules, thereby isolating the variant single-stranded nucleic acid molecule. Similarly, certain embodiments embrace labeling the 5'-end of the variant single-stranded nucleic acid molecule with a detectable label to facilitate the identification and isolation of said molecule in, e.g., size fractionation methods such as the WAVE® System platform (Transgenomic, Omaha, Nebr.) or gel electrophoresis. For example, the preparative capability of the WAVE System platform can be employed by injecting the denatured product into the WAVE System for analysis and collection of the peak corresponding to the labeled variant nucleic acid molecule. Detectable labels can include, e.g., biotin, a fluorophore, a chromophore or the like. Such labels can be incorporated into the variant nucleic acid molecule using conventional methods, e.g., using a labeled universal primer. Alternatively, FIG. 2B shows that when the reference molecule is bound to a solid support, the variant single-stranded nucleic acid molecule can be obtained free in solution. Because the variant single-stranded nucleic acid molecule illustrated in FIG. 2B is found in solution with a 3'-capped reference molecule, "isolated" or "isolating" in the context of this method step does not preclude the presence of other molecules. However, it is desirable that when other molecules are present, said other molecules do not participate, inhibit, or alter subsequent method steps.

Subsequently, a Double-Stranded Linker, containing a 3'-overhang, is ligated to the 3'-end of the mismatch-specific endonuclease cleavage product. In so far as the mismatch-specific endonuclease cleavage product can be double-stranded or denatured to yield a single-stranded product (see FIG. 1), the Double-Stranded Linker is ligated to at least the 3'-end of the strand with the one or more variant nucleotides. Specific features of the Double-Stranded Linker are depicted in FIG. 1 and include: a duplex DNA composed of two complementary oligonucleotides, wherein this complementary or double-stranded portion is of a predetermined sequence (e.g., a universal sequence of approximately 6 to 50 nucleotides); a 3'-overhang on the lower strand of the duplex composed of 1, 2, 3, 4, 5, or 6 nucleotides, wherein the overhang is degenerate in nature so that the linker can ligate to all possible cleavage sites; a phosphorylated 5'-end on the upper strand of the duplex; and optionally the 3'-end of the upper strand or the 3'-end of the lower strand are blocked or capped (e.g., with a 3'-amino functional group or ddNTP) to prevent further ligation. Alternatively, the 3'-end of the lower strand can remain free such that it can be extended later by a polymerase. Optionally, a functional group such as biotin can be included on the upper strand of the linker so that it can be captured easily with, e.g., Streptavidin-coated surfaces. Moreover, particular embodiments embrace a linker with a hairpin structure (See FIG. 3).

Such Double-Stranded Linkers have been described in the art for use in randomized terminal linker-dependent PCR (RD-PCR) detection of DNA damage. See, e.g., Zhang & Heng (2002) *Biomed. Environ. Sci.* 15:203-8; Rao, et al. (2005) *J. Sichuan Univ.* (*Med. Sci. Edi.*) 36:779-781; Wu & Heng (2006) *J. Sichuan Univ.* (*Med. Sci. Edi.*) 37:33-34. When employing a two nucleotide 3'-overhang on the Double-Stranded Linker, a mixture of just 16 molecules would be required, while 3 nucleotides would require 64 molecules, and 4 nucleotides would require 256 molecules. It is contemplated that as many as 6 degenerate nucleotides (i.e., 4096 molecules) can be employed as equal concentrations are not essential. However, in particular embodiments, a two or three nucleotide 3'-overhang is employed. In this regard, a kit containing a double-strand linker with a three nucleotide 3'-overhang could include a mixture of the double-stranded molecules, e.g., as exemplified below.

```
                                   (SEQ ID NO:1)
5'-P-TGT AAA ACG ACG GCC AGT-3'-Blocker

                                   (SEQ ID NO:2)
Blocker-3'-NNN ACA TTT TGC TGC CGG TCA-5'
```

The linker can be ligated to the newly exposed 3'-OH groups (i.e., generated by the mismatch-specific endonuclease) using standard ligation conditions. Such conditions can include the use of the enzyme T4 DNA ligase together with ATP and other components well-known in the art.

Figure 3:
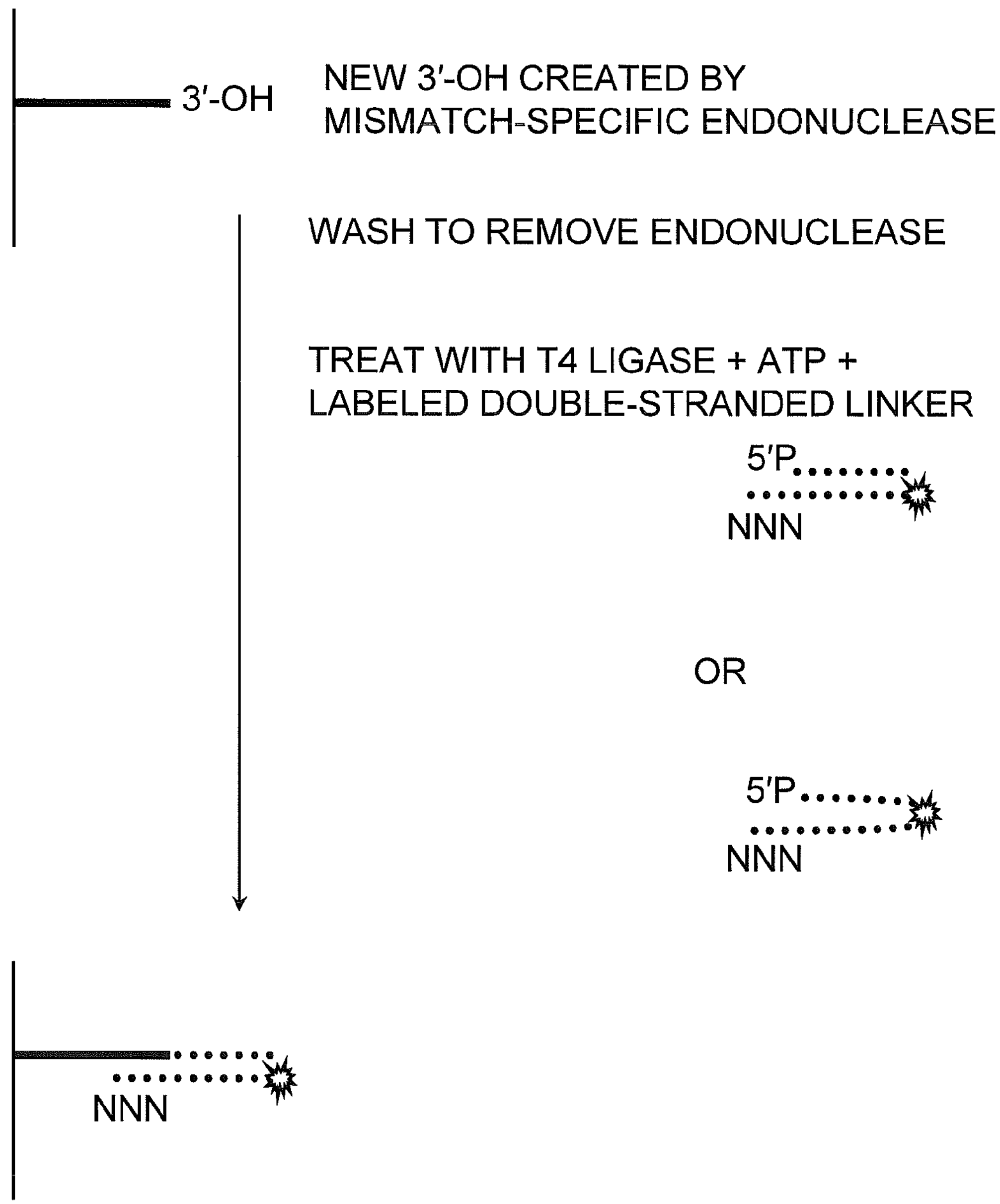
FIG. 3 depicts the use of a labeled linker and a labeled linker with a hairpin for ligation to the variant nucleotide 3' end (v) created by cleavage.

In some embodiments of the present invention, the Double-Stranded Linker is detectably labeled (See FIG. 3). In this regard, the linker contains a label (e.g., a fluorophore or a moiety commonly used in ELISA, such as a biotin functional group which can bind to a Streptavidin-horseradish peroxidase conjugate) allowing detection at a low concentration. Ligation of the labeled linker to the newly generated 3'-OH end of an immobilized variant nucleic acid molecule can provide for rapid detection of the presence of a mutation. In this regard, mutations can be detected in batch mode, e.g., by flow-cytometry or an array, permitting high-throughput analysis.

Advantageously, the attached linker is immediately adjacent to the variant nucleotide(s) in the variant single-stranded nucleic acid molecule and provides a means to readily detect and determine the nature of the variant (s). It is contemplated that the resulting linker-ligated variant nucleic acid molecule can be denatured and isolated (e.g., via the WAVE System as described herein), or alternatively, the linker-ligated variant nucleic acid molecule can be directly used in PCR and/or sequence reactions. There are a variety of methods which can be used to determine the sequence of the one or more variant nucleotides in the variant nucleic acid molecule. For example, when the starting material is generated by PCR amplification, as disclosed herein, it is contemplated that single-template PCR methods can be employed in combination with conventional sequencing methods to reveal the sequence of the variant nucleotide(s). In accordance with such PCR amplification of the variant nucleic acid molecule, some embodiments embrace the use of two different universal PCR primers, whereas other embodiments embrace the use of a single universal PCR primer which anneals to both the 5'- and 3'-end. Single-template PCR methods, e.g., polony PCR, are known in the art. See, e.g., Mitra & Church ((1999) *Nucleic Acids Res.* 27:e34) and Mitra, et al. ((2003) *Proc. Natl. Acad. Sci. USA* 100:5926-5931), wherein each PCR product that arises represents a homogeneous "plonal" product (by analogy to PCR clonal).

Linker-ligated variant nucleic acid molecules or PCR amplicons of the same can be analyzed by Sanger sequencing, PCR-based sequencing or sequencing with a mixture of tagged probes (e.g., fluorescence, mass-tags, etc).

Alternatively, certain embodiments embrace identifying the sequence of the variant nucleotide(s) in a nucleic acid molecule by sequencing-by-synthesis methods such as pyrosequencing, GENOME SEQUENCE 20 DNA sequencing system (GS20, Roche/454 Life Sciences; Margulies, et al. (2005) *Nature* 43:376-380), or Solexa sequencing (Illumina; Robertson, et al. (2007) *Nat. Methods.* 4(8):651-7). In pyrosequencing, a primer that is complementary to the predetermined linker sequence is annealed to the linker-ligated variant nucleic acid molecule and the first of four deoxynucleotide triphosphates (dNTP) is added to the reaction. DNA polymerase catalyzes the incorporation of the deoxynucleotide triphosphate into the DNA strand, if it is complementary to the base in the template strand. Each incorporation event is accompanied by release of pyrophosphate (PPi) in a quantity equimolar to the amount of incorporated nucleotide. ATP sulfurylase quantitatively converts PPi to ATP in the presence of adenosine 5' phosphosulfate. This ATP drives the luciferase-mediated conversion of luciferin to oxyluciferin that generates visible light in amounts that are proportional to the amount of ATP. The light produced in the luciferase-catalyzed reaction is detected by a charge-coupled device (CCD) camera and seen as a peak in a PYROGRAM, wherein each light signal is proportional to the number of nucleotides incorporated. Apyrase, a nucleotide degrading enzyme, continuously degrades unincorporated dNTPs and excess ATP. When degradation is complete, another dNTP is added. Addition of dNTPs is performed one type at a time. As the process continues, the complementary DNA strand is built up and the nucleotide sequence is determined from the signal peak in the PYROGRAM. Because the mutation is immediately adjacent to the linker, sequence analysis of 100 bp would be sufficient to both identify the sequence of the SNP or mutation and identify the location of the variant nucleic acid molecule in the genome or gene. The Solexa sequencing-by-synthesis platform uses reversibly terminated, fluorescently labeled dNTPs to sequence immobilized DNA templates in massively parallel fashion. It is contemplated that gene or genome-wide analysis can be performed using the instant method in combination with a massively parallel sequence-by-synthesis format.

Figure 4:
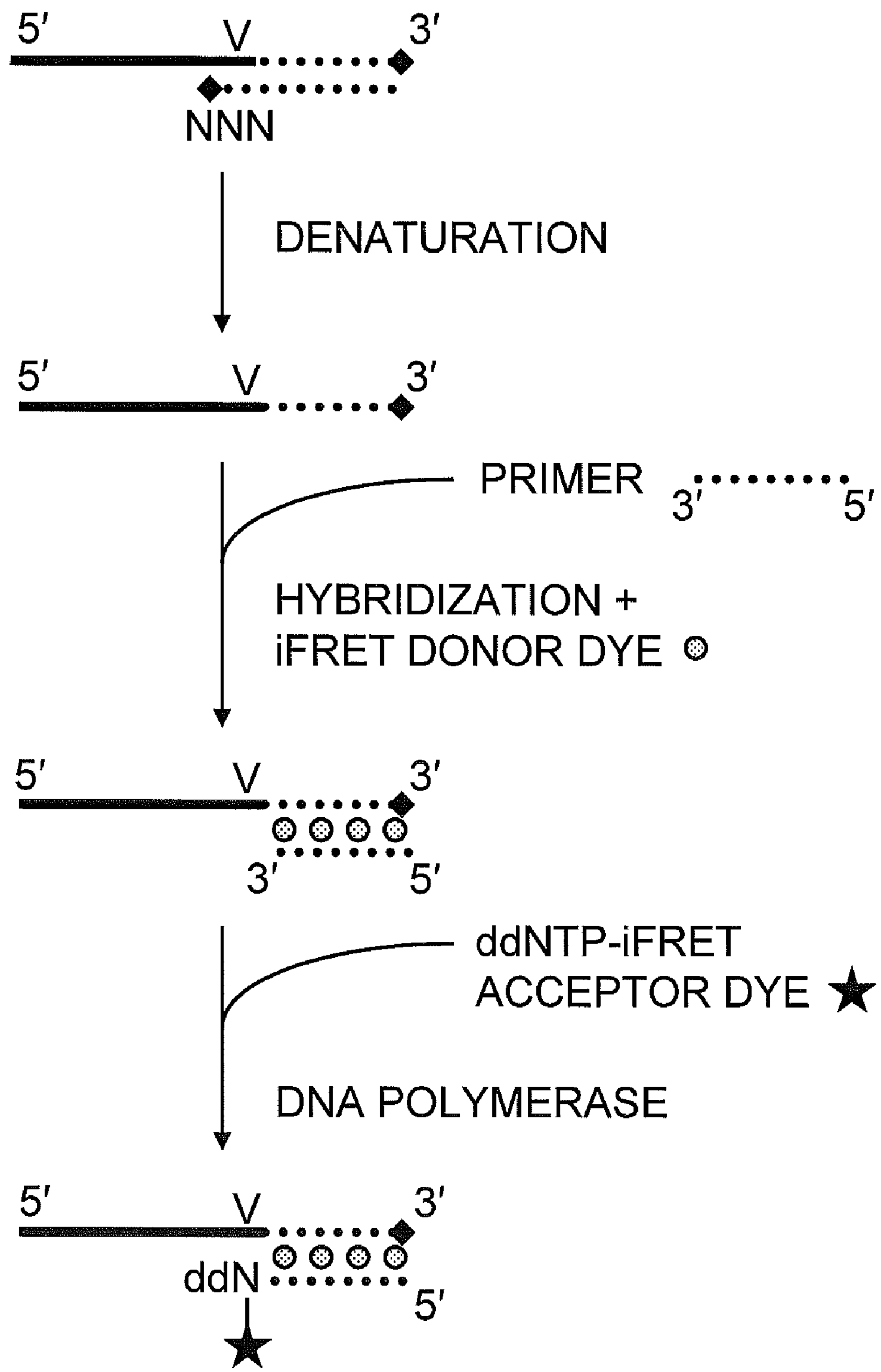
FIG. 4 shows a schematic of a single-base extension approach to determining the sequence of a variant nucleotide (V) adjacent to a linker.

In still other embodiments, the sequence of the variant nucleotide in a nucleic acid molecule is identified using a single-base extension or mini-sequencing approach (see, e.g., Takatsu, et al. (2004) *Nucleic Acids Res.* 32:e156). As depicted in FIG. 4, this approach involves denaturing the double-stranded portion of the linker, which is ligated to the single-stranded variant nucleic acid molecule and hybridizing a complementary primer to the predetermined linker sequence in the presence of an intercalating fluorescence resonance energy transfer (FRET) donor such as SYBR green I. Subsequently, the FRET donor-labeled molecule is contacted with DNA Polymerase and a mixture of ddCTP, ddATP, ddTTP and ddGTP, each labeled with a different FRET acceptor (e.g. ROX or Cy5), to extend the complementary primer. Depending on the nucleotide incorporated, a different wavelength of light will be emitted (i.e., base-specific fluorescence) and therefore reveal the sequence of the variant nucleotide. For example, ROX emits an orange fluorescence upon excitation by the green light emitted by SYBR Green I, whereas red fluorescence is emitted from Cy5 upon excitation by SYBR Green I.

Still other embodiments provide that the variant nucleotide(s) is determined by:

(i) PCR amplification of the nucleic acid molecule using a primer specific to the molecule and another primer specific to the predetermined linker sequence, and (ii) sequencing by termination using either a sequencing primer specific to the predetermined Double-Stranded Linker, or specific to the nucleic acid molecule.

When the identification of more than one variant nucleotide is required, additional primers can be used in combination with a single-base extension approach. For example, on the basis of the nucleotide revealed by the first primer extension reaction, a subsequent, overlapping primer can be generated with one base more on its 3'-end which is complementary to the revealed nucleotide. There are four possibilities A, C, G or T thereby requiring only a modest increase in the number of extended primers which need to be generated. The next nucleotide can then be determined, wherein the process can be repeated with sixteen primers, and sixty four primers, etc. When applied sequentially and on the basis of the previous bases revealed, four steps using four primers will reveal the four bases at the 3'-OH end of the variant nucleic acid molecule.

The key novelty of the instant invention is the extension of the variant nucleotide itself, with a known sequence. This juxtaposition of the variant to the Double-Stranded Linker readily allows rapid processing by PCR and/or sequence analysis. While the prior art provides various methods for extending 3'-ends, including blunt-end ligation with a linker (see, U.S. patent application No. 2003/0022215) and the use of terminal transferase enzyme to extend the 3'-OH by polymerization with deoxynucleotide-triphosphates, the present invention is distinct because mismatch-specific endonucleases create a 3'-OH overhang, such that the conventional creation of blunt-ends for ligation of a linker would actually remove the variant nucleotide of interest. Thus, while the relative location of the mutation could be identified, the sequence of the variant nucleotide could not be determined. Moreover, the yield of blunt-end ligation is lower than that of ligation to overhangs. A disadvantage of using terminal transferase is that a homopolymer of undefined length is created at the 3'-end leading to a range of fragment sizes in subsequent processes such as PCR and sequencing. Moreover, it would be nearly impossible to know from sequence analysis where the homopolymer begins if the cleavage site itself contains the same base as that used for creating the extension.

While regular Sanger sequencing can be employed in the present methods, the use of sequencing-by-synthesis methods has particular utility in combination with the present methods because the limitations of shorter read lengths of sequencing-by-synthesis technologies is not a handicap. If, for example, pyrosequencing is employed, approximately 25 rounds of pyrosequencing would be sufficient to identify the variant nucleotide and its context. In this regard, the prior art does not provide this integration of minimal sequencing with mismatch-specific endonuclease cleavage. As such, the present methods find application in SNP detection, mutation detection, methylation detection (after bisulfite treatment of genomic DNA), detecting variation between alleles, between individuals, between normal and diseased tissue, between species and for detection of induced mutations.

Moreover, it is contemplated that the instant methods can be employed in a whole gene application where the number of variations expected is limited in number, wherein many amplicons covering all exons and promoter sites could be mixed together. The mixture could be achieved by multiplex PCR using a universal primer or could be mixed just prior to attachment of the linker Using the solid-phase approach (i.e., the use of a solid support) there will only be one cleavage product per variant and no intact uncleaved fragment. A single injection onto a WAVE System can be used to reveal all variants in one or more genes. The nucleic acid molecules in the separated peaks can be collected and cycle-sequenced or subjected to pyrosequencing or other highly parallel sequencing-by-synthesis methods. The results can be used to identify the gene location from which the cleavage fragment originated and the variation present at the location adjacent to the linker.

In addition, the present method can be adapted to generate genomic libraries of nucleic acid molecules with mismatches. The ability to harness all the genetic changes between any two given genomes or within a set of genomes provides information as to the causes or predisposition to human disease and the development of diagnostic or prognostic assays. Additionally such data would add to the understanding of cellular biochemistry with regard to variations in metabolic pathways, response to the environment and development of organisms. Conventional assays can identify these changes, however, they are closed assays, i.e., they often require prior knowledge of the variation, must be targeted to a particular genetic locus or group of loci, or require massive amounts of DNA sequencing to identify the variation.

In contrast, a method is provided herein to generate libraries of genetic variations present within a DNA population, without prior knowledge of the variation. A mismatch-specific DNA endonuclease is used to cleave target DNA at sites of single-base variations and insertion/deletions allowing the variations to be placed contiguous to a Double-Stranded Linker of known sequence. The Double-Stranded Linker is then used to direct DNA sequence identification of the variation.

The present invention circumvents the limitations in the art by providing an open assay for assembling a complete collection of genetic variations in their natural sequence contexts in a readily accessible form, excluding non-variant DNA sequences at the same time. Accordingly, the present invention greatly facilitates the process of comparative genome analysis and disease marker genotyping.

Libraries can be established independent of, or in bacterial cells. The cell-independent library can be queried to identify all such heterozygous variations in a DNA sample by massively-parallel sequencing of individual DNA molecules (e.g., by using the Genome Sequencer FLX System and protocols developed by 454 Life Sciences and Roche) using a Universal DNA Sequencing Primer. Alternatively, the library can be queried to identify a variation at any single genetic locus of a DNA sample by locus-specific PCR followed by classical termination sequencing using a Universal DNA Sequencing Primer. The cell-dependent library can be queried to identify all such haploid variations in a low complexity DNA sample (viral or isogenic bacterial populations) by classical termination sequencing of individual colony DNA using flanking vector DNA sequencing primers.

Comparisons of variations between samples taken from diseased versus healthy individuals will link the disease to the genetic differences observed. In a similar manner, comparison of genetic variations in libraries from different microorganisms or viruses is used to establish an association between a particular phenotype and a genetic change in their DNA.

Libraries of genetic variations are generated by (a) fragmenting one or more samples of genomic DNA;

(b) denaturing and annealing the fragmented genomic DNA to generate double-stranded genomic DNA molecules, wherein one strand of said double-stranded genomic DNA molecules has one or more variant nucleotides which create at least one mismatch in the double-stranded genomic DNA molecules;

(c) blunt ending, dephosphorylating 3' ends, and phosphorylating 5' ends of the double-stranded genomic DNA molecules;

(d) ligating a Double-Stranded Adaptor onto ends of the double-stranded genomic DNA molecules, wherein said Double-Stranded Adaptor contains a restriction enzyme cut site and a functional group at one 5' end;

(e) size fractionating the double-stranded genomic DNA molecules of step (d) to remove Double-Stranded Adaptor;

(f) immobilizing the size fractionated, double-stranded genomic DNA molecules via binding of the functional group of the Double-Stranded Adaptor to reactive groups of a first solid support;

(g) removing double-stranded genomic DNA molecules which are not immobilized at both ends by the first solid support;

(h) contacting the immobilized double-stranded genomic DNA molecules with a mismatch-specific endonuclease so that the double-stranded genomic DNA molecules are cleaved at the 3'-side of the mismatches therein;

(i) ligating a Double-Stranded Linker to the 3'-end of the immobilized genomic DNA molecules, wherein the double-stranded portion of the linker is of a predetermined sequence and the Double-Stranded Linker is composed of: an upper strand generated from a single oligonucleotide with a phosphate at the 5' end and a blocking group at the 3' end; and a lower stranded generated from two oligonucleotides, a short oligonucleotide with a portion complementary to the upper strand and a degenerate portion at the 3' end which creates a 3'-overhang and is blocked at the 3' end, and a longer complementary oligonucleotide with a functional group at the 5' end and a 3'-OH, wherein the two oligonucleotides of the lower strand create a nick;

(j) repairing the nicked DNA of the product of step (i) by *E. coli* DNA polymerase I-catalyzed nick translation;

(k) immobilizing the Double-Stranded Linker ligated to the immobilized double-stranded genomic DNA molecules via binding of the functional group of the Double-Stranded Linker to reactive groups of a second solid support;

(l) contacting the product of step (k) with a restriction enzyme which cleaves the Double-Stranded Adaptor at the restriction enzyme cut site thereby releasing the double-stranded genomic DNA molecules from the first solid support and creating a library of genomic DNA molecules with genetic variations attached to the second solid support; and (m) releasing single-stranded DNA molecules with genetic variations from the second solid support by alkaline treatment.

The resulting single-stranded genomic DNA molecules of this method can then be analyzed in a variety of ways. For example, the single-stranded DNA can be sequenced via sequencing-by-synthesis methods such as pyrosequencing and GENOME SEQUENCE 20 DNA sequencing system (GS20, Roche/454 Life Sciences; Margulies, et al. (2005) supra), wherein the predetermined sequence of the Double-Stranded Linker of step (j) is hybridized to a complementary primer used in such sequencing methods. Alternatively, it can be determined whether a variant nucleotide is present in a particular genomic location. This can be achieved by combining a primer, complementary to the Double-Stranded Linker of step (j), with a gene-specific primer in an amplification reaction, wherein the synthesis of an amplification product indicates that a variant nucleotide is present in that particular genomic location. As a further alternative, the single-stranded genomic DNA molecules can be made double-stranded, cloned into a vector, and sequenced by conventional sequencing methods, e.g., Sanger sequencing.

In accordance with this method of the invention, samples of genomic DNA can be from a single genome or from more than one genome, e.g., a reference genome or test genome, wherein the sequence of the reference genome is known or does not contain variant nucleotides and the sequence of the test genome is unknown or contains variant nucleotides for which it is desirable to know the location of said variant nucleotides. Genomic DNA can be obtained from any source including prokaryotes, eukaryotes (e.g., fungi, or plants), viruses and the like. Moreover, genomic DNA can be obtained from two genetically related individuals or two individuals with a high degree of genetic variability.

Fragmentation of the sample(s) of genomic DNA can be carried out using any conventional method. Desirably, fragmentation is carried out under a controlled, random manner by, e.g., nebulization, sonication, or enzymatic fragmentation. Once fragmented, the genomic DNA is then denatured, e.g., by heating the DNA, and subsequently annealed under standard conditions to generate double-stranded genomic DNA molecules. Wherein one strand of the resulting double-stranded heteroduplex genomic DNA molecules has one or more variant nucleotides as compared to the other strand, mismatches are created in the double-stranded genomic DNA molecules.

Subsequently, the double-strand genomic DNA molecules are treated under appropriate conditions to produce blunt ends, which are dephosphorylated at the 3' ends and phosphorylated at the 5' ends. By way of illustration, the double-stranded genomic DNA molecules can be treated with T4 DNA polymerase and Klenow fragment DNA polymerase in the presence of dNTPs to create blunt ends. Furthermore, the double-strand genomic DNA molecules can be contacted with T4 polynucleotide Kinase in the presence of ATP to transfer the γ-phosphate of ATP to the 5'-OH of the double-strand DNA molecules and remove 3' phosphates. In addition, any nicks present in the double-strand genomic DNA molecules can be repaired with a ligase such as *E. coli* DNA ligase.

As generally discussed supra, attachment of a nucleic acid molecule to a solid support can be accomplished using an adaptor modified with a function group. In accordance with the particular embodiments of generating the present library, a Double-Stranded Adaptor containing a restriction enzyme cut site and a functional group at the 5' end of one strand is ligated to the double-stranded genomic DNA molecule. This ligation step places a known sequence at both ends of the double-stranded genomic DNA molecules and further provides a functional group at free 5' ends.

The restriction enzyme cut site of the Double-Stranded Adaptor is generally located at a suitable distance from the end with the functional group so that when bound to a solid support, the solid support does not interfere with restriction enzyme cutting. The restriction enzyme cut site is also at a suitable distance from the other 5' end to leave approximately 20 bp to 25 bp after cutting so that a PCR primer could hybridize.

Desirably, the restriction enzyme cut site is recognized and cleaved by a restriction enzyme expected to have infrequent cut sites in the double-strand genomic DNA molecules. Such enzymes include those with seven- or eight-nucleotide cut site sequences and enzymes whose cut site sequences contain motifs that are rare in the target DNA. Examples of restriction enzymes with seven- or eight-nucleotide recognition sequences include, e.g., SapI and SgfI. Genomic DNA molecules do not have random sequences and some are significantly deficient in certain motifs. For example, the sequence 5'-CG-3' is rare in human DNA. Thus, restriction enzymes that recognize a cut site containing 5'-CG-3', cut human DNA relatively infrequently. Examples of such enzymes include SmaI, which cuts human DNA on average once every 78 kb, and BssHII, which cuts once every 390 kb. NotI, an eight-nucleotide cutter, also targets 5'-CG-3' sequences and cuts human DNA very rarely, approximately once every 10 Mb. Alternatively, genomic DNA can be methylated before Double-Stranded Adaptors are ligated with a methyl transferase that prevents the restriction enzyme from cutting the genomic DNA.

Subsequent to the ligation of a Double-Stranded Adaptor, the double-stranded genomic DNA molecules are size fractionated to remove adaptor. Size fractionation can be carried out using any suitable method including, but not limited to, gel filtration (e.g., SEPHACRYL S-300 HR or S-400 HR).

The size fractionated double-stranded genomic DNA molecules is then immobilized on a first solid support by binding of the functional group of the Double-Stranded Adaptor to reactive groups of the first solid support (e.g., a membrane, bead, column, particle, gel, etc.). As discussed herein, functional group and reactive group interactions can include covalent and non-covalent bonds. Examples of such interactions include antibody-antigen and receptor-ligand. One specific example routinely used in the art is biotin-Streptavidin. Advantageously, only DNA molecules with a Double-Stranded Adaptor ligated at one or both ends will bind to the first solid support. As such, DNA molecules which are not immobilized by the first solid support are removed by, e.g., washing the solid support with a suitable buffer that does not disrupt binding to the solid support and further degrading DNA which does not have both ends of the DNA bound to the solid support. Degradation of DNA molecules without both ends bound to the first solid support can be carried out by treatment with exonuclease V.

The immobilized double-stranded genomic DNA molecules are subsequently contacted with a mismatch-specific endonuclease so that the double-stranded genomic DNA molecules are cleaved at the 3'-side of the mismatches therein. As discussed herein mismatch-specific endonucleases such as CEL I and CEL II (i.e., SURVEYOR® Nuclease) cleave DNA at single-base and small indel mismatches leaving a 3'-OH overhang containing the mismatch base(s). Wherein nicks may be produced by the mismatch-specific endonuclease, specific embodiments provide for simultaneous treatment of the double-stranded genomic DNA molecules with Taq DNA ligase and NAD to seal nicks produced by the mismatch-specific endonuclease at non-mismatch sites.

As in the other methods of the invention, the one or more variant nucleotides of the double-stranded genomic DNA molecules are tagged by ligating a Double-Stranded Linker to the 3'-end of the immobilized genomic DNA molecules. As described herein, one strand of the Double-Stranded Linker contains a nick, has a degenerate sequence at the 3' end, wherein the degenerate sequence is a 3'-overhang, and the double-stranded portion of the linker is of a predetermined sequence. An additional feature of the Double-Stranded Linker of this method is that the strand with the degenerate sequence at the 3' end also has a functional group at the 5' end. It is contemplated that this functional group can be the same as or different from the functional group used in the Double-Stranded Adaptor of step (d). In embodiments embracing the use of the same functional group in the Double-Stranded Linker and Double-Stranded Adaptor, free reactive groups of the first solid support can be blocked to eliminate binding of the Double-Stranded Linker to the first solid support. By way of illustration, unoccupied biotin binding sites on a Streptavidin-coated bead can be occupied with free biotin to prevent binding of a biotinylated Double-Stranded Linker. The structure of an exemplary Double-Stranded Linker used in step (i) is shown in FIG. 6.

Subsequent to ligating the Double-Stranded Linker to the double-stranded genomic DNA molecules, the immobilized DNA is treated with one or more enzymes to repair nicked DNA. For example, the 5'-to-3' exonuclease activity and DNA polymerase activity of *E. coli* DNA Polymerase I (Pol I) in the presence of dNTPs can be used to repair DNA by nick translation.

According to the next step of the method, exposed 5' ends of the Double-Stranded Linker are immobilized via binding of the functional group of the Double-Stranded Linker to reactive groups of a second solid support. Wherein the Double-Stranded Linker and Double-Stranded Adaptor employ the same functional group, the second solid support and first solid support can be the same solid support. Conversely, when a different functional group is used in the Linker and Adaptor, the reactive group of the first and second solid supports can also be different. Because steps (h) through (k) of this method can be repeated one or more times to ensure that increasing proportions of mismatches are tagged with the Double-Stranded Linker, immobilization of the exposed 5' ends of the Double-Stranded Linker to a solid support will protect the ends from any exonuclease activity, e.g., that of SURVEYOR Nuclease.

To remove any DNA that was not cut by the mismatch-specific endonuclease and labeled with a Double-Stranded Linker, the DNA is treated with a restriction enzyme which cleaves the Double-Stranded Adaptor at the restriction enzyme cut site. As a result, only double-stranded genomic DNA molecules with a Double-Stranded Linker attached thereto will be immobilized, i.e., to the second solid support, and recovered after washing.

The resulting immobilized double-stranded genomic DNA molecules represent a library of genomic DNA molecules containing genetic variations which are tagged. As discussed herein, the library can be analyzed via a variety of methods including PCR amplification and sequencing to identify the location and sequence of the genetic variations. In certain embodiments, subsequent analysis requires a single-stranded molecule such that the method can further include the step of (n) denaturing the double-stranded genomic DNA molecule to create a library of single-stranded genomic DNA molecules with tagged variant nucleotides.

The invention is described in greater detail by the following non-limiting examples.

EXAMPLE 1

Materials and Methods

Materials. SURVEYOR Nuclease (CEL II) was purified from celery by a modification of known methods (Yang, et al. (2000) supra; Gerard, et al. (2006) supra). Enzymatic activity was assigned based upon a denatured DNA solubilization assay performed at pH 8.5 (Yang, et al. (2000) supra). One unit of solubilization activity was defined as the amount of enzyme required to produce 1 ng of acid-soluble material in 1 minute at 37° C.

OPTIMASE® Polymerase and MAXIMASE™ Polymerase were from Transgenomic, Inc (Omaha, Nebr.). M-280 Streptavidin magnetic DYNABEADS® were from Dynal Biotech (INVITROGEN, Carlsbad, Calif.). Cloned T4 DNA ligase was prepared by Transgenomic, Inc. Streptavidin was purchased from SIGMA (Sigma/Aldrich, St. Louis, Mo.). Control G and Control C plasmids were from Transgenomic, Inc. Control C and Control G have inserts (632 bp) that differ at a single base pair, so that annealing of their PCR products produces heteroduplices that when cleaved by SURVEYOR Nuclease produce cleavage products 415 and 217 bp long.

Oligonucleotides. Oligonucleotides were synthesized by Sigma-Genosys (The Woodlands, Tex.). Unless indicated otherwise, oligonucleotides were desalted before use.

Oligonucleotides used in the study included: pCEL190F30, 5'-ACA CCT GAT CAA GCC TGT TCA TTT GAT TAC-3' (SEQ ID NO:3); pCEL190F30-5'Bio, 5'-Biotin-ACA CCT GAT CAA GCC TGT TCA TTT GAT TAC-3' (SEQ ID NO:4); pCEL81OR25, 5'-CCA AAG AAT GAT CTG CGG AGC TTC C-3' (SEQ ID NO:5); pCEL81OR25-5'Bio, 5'-Biotin-CCA AAG AAT GAT CTG CGG AGC TTC C-3' (SEQ ID NO:6); M13RDPCRtop, 5'-$P0_4$-CGA CTG GAG CAC GAG GAC ACT ACT GGC CGA CGT TTT ACA CC—$NH_4^+$-3' (SEQ ID NO:7); M13RDPCR3Nbottom, 5'-GGT GTA AAA CGA CGG CCA GTA GTG TCC TCG TGC TCC AGT CGN NN—$NH_4^+$-3' (SEQ ID NO:8); M13RDPCR2Nbottom, 5'-GGT GTA AAA CGA CGG CCA GTA GTG TCC TCG TGC TCC AGT CGN N—$NH_4^{+-}$3' (SEQ ID NO:9); M13RDPCR1Nbottom, 5'-GGT GTA AAA CGA CGG CCA GTA GTG TCC TCG TGC TCC AGT CGN—$NH_4^{+-}$3' (SEQ ID NO:10); M13uniPCR, 5'-GGT GTA AAA CGA CGG CCA GTA GTG TCC TCG TG-3' (SEQ ID NO:11); pCEL324F21, 5'-CCA TGG TAA GGA TAT GCA CTC-3' (SEQ ID NO:12); pCEL490R22, 5'-GAG TTT CGC CAG ATT CAA CAT C-3' (SEQ ID NO:13). Triple degenerate linkers are sufficient for ligation to all possible sites, however a mixture of single, double and triple degenerate linkers was used in this protocol.

PCR Amplification Conditions of DNA for Annealing and Binding to Streptavidin Magnetic Beads. A 632-bp region from Control C or Control G plasmid was amplified using 10 ng of template (either Control C or Control G plasmid), 66 ng of pCEL190F30-5'Bio, 33 ng of pCEL190F30, 66 ng of pCEL81OR25-5'Bio, 33 ng of pCEL810R25, 0.2 mM of each dNTP, and 0.5 μL of OPTIMASE Polymerase (6 U/μL) in 1× OPTIMASE Reaction Buffer (10 mM Tris-HCl, pH 8.8, 75 mM KCl, 1.5 mM $MgCl_2$, and 0.01% (v/v) TRITON X-100).

Amplification of Ligated Cleavage Products Eluted from Streptavidin Magnetic Beads. The 418-bp fragment upstream from the SURVEYOR Nuclease cleavage site in Control G/C heteroduplices was amplified using 1 μL of ligation reaction mix as template, 100 ng of pCEL190F30, 100 ng of M13uniPCR, 0.2 mM of each dNTP, and 0.5 μL OPTIMASE Polymerase (6 U/μL) in 1× OPTIMASE Reaction Buffer. The 216-bp fragment downstream from the SURVEYOR Nuclease cleavage site in Control G/C heteroduplices was amplified using 1 μL of ligation reaction mix as template, 100 ng of pCEL81OR25, 100 ng of M13uniPCR, 0.2 mM of each dNTP, and 0.5 μL of OPTIMASE Polymerase (6 U/μL) in OPTIMASE Polymerase Buffer.

PCR Amplification Cycling Parameters. PCR amplifications were carried out in a heated-lid thermocycler using the following program: 95° C. for 2 minutes; 30 cycles of 95° C. for 30 seconds, 63.8° C. for 30 seconds, and 72° C. for 70 seconds; and finally 72° C. for 5 minutes.

Annealing of Amplified PCR Products. Annealing, using a thermocycler, was performed as follows. Equal amounts of Control C and Control G PCR products in PCR reaction components were mixed; denatured at 95° C. for 2 minutes and cooled at a rate of −2° C./second until the temperature reached 85° C., and then cooled at a rate of −0.1° C./second to 25° C. Samples were then held at 4° C.

Binding of Amplified, Annealed PCR Products to Streptavidin Magnetic Beads. Annealed Control G/C PCR products (10 μL; ~400 ng) were mixed with 10 μL of 10 mg/mL M-280 Streptavidin DYNABEADS magnetic beads stabilized in 2 M NaCl and 10 mM Tris-HCl (pH 8) and incubated at room temperature for 10 minutes. Samples were then washed twice with 40 μL of 1M NaCl and 5 mM Tris-HCl (pH 8) and twice with 40 μL of 1× OPTIMASE Reaction Buffer, and resuspended in 20 μL of 1× OPTIMASE Reaction Buffer.

SURVEYOR Nuclease Digestion. Annealed Control G/C PCR products (200 ng) in 1× OPTIMASE Reaction Buffer were incubated in the presence of 1.5 mM or 10 mM $MgCl_2$ (as indicated), 1 μL of SURVEYOR Nuclease (5 U/μL) and 1 μL of T4 DNA ligase (ENHANCER S) at 42° C. for 20 minutes. Digestion was stopped with 1/10 volume of 0.5 M EDTA (pH 8.0) and the DNA present in the supernatant was precipitated with 3 volumes of ethanol and resuspended in 10 μL of 1 mM Tris-HCl and 0.1 mM EDTA (pH 8).

Linker Preparation M13RDPCRtop (15 μg), 5 μg M13RDPCR3Nbottom, 5 μg M13RDPCR2Nbottom and 5 μg M13RDPCRINbottom were mixed in 50 mM NaCl, 10 mM Tris-HCl (pH 8), and 1 mM EDTA (pH 8) to a final concentration of 0.91 μg/μL. The mixture was denatured at 94° C. for 4 minutes, cooled at a rate of −0.1° C./second until the temperature reached 73° C., kept at 73° C. for 30 minutes and cooled at a rate of −0.1° C./second until the temperature reached 16° C.

Ligation of Digested DNA and Linker. SURVEYOR Nuclease-digested DNA samples (5 μL; 50-100 ng) were mixed with 560 ng of linker and 400 units (cohesive end ligation units) of T4 DNA ligase (400 U/μL) in ligation buffer (66 mM Tris-HCl, pH 7.6, 10 mM $MgCl_2$, 1 mM ATP, 1 mM DTT) containing 7.5% (w/v) PEG 6000 in a final volume of 20 μL and incubated at 16° C. for 60 minutes. Ligation was stopped by incubation at 65° C. for 10 minutes.

DNA Sequence Analysis. The 415-bp and the 217-bp fragments produced by SURVEYOR Nuclease cleavage of Control G/C heteroduplices were ligated to linker and amplified as described herein. Each amplified DNA was purified by using a QIAQUICK PCR Purification Kit (QIAGEN, Valencia, Calif.), Quick-Step PCR Clean-up System (Edge BioSystems, Gaithersburg, Md.) or was isolated by subjecting the DNA to agarose gel electrophoresis (1.75% (w/v) agarose), cutting the DNA band from the gel, and cleaning up the DNA using a QIAGEN Gel Clean-up System (QIAGEN, Inc., Valencia, Calif.). Purified DNA fragments (20 ng) were subjected to cycle sequencing using 2.5 pmole of primer pCEL324F21, pCEL190F30, pCEL490R22, or pCEL81OR25, 5 μL Better DAF5 Buffer (The Gel Company, San Francisco, Calif.), and 0.5 μL Big Dye Mix (Applied Biosystems, Foster City, Calif.). Reactions were denatured at 95° C. for 4 minutes followed by 25 cycles of 95° C. for 30 seconds, 54° C. for 1 minute and 72° C. for 4 minutes, and then extended at 72° C. for 5 minutes. Sequencing products were purified using CLEAN-SEQ magnetic beads (Agencourt, Beverly, Mass.) according to the manufacturer's instructions and analyzed in a 3100 Genetic Analyzer (Applied Biosystems, Foster City, Calif.).

Example 2

Capturing 3'-Overhang Nucleotides Generated by Mismatch Endonuclease Using Randomized Terminal Linker-Dependent PCR Requirements for Capturing the 3'-Overhang Nucleotides Generated by SURVEYOR Nuclease at Mismatch Cut Sites. Direct sequence analysis of SURVEYOR Nuclease cleavage products involves the capture of the 3'-overhangs created after digestion at a mismatch site. The capture must be specific to eliminate background during the subsequent sequencing reaction. The main challenge comes from background produced as the result of the 5'-to-3' exonuclease activity of SURVEYOR Nuclease (Gerard, et al. (2006) supra) attacking the ends of PCR products. After digestion of a Control G/C heteroduplex with SURVEYOR Nuclease, cleavage fragments (415 bp and 217 bp) are present in a mixture along with undigested homoduplices and heteroduplices (632 bp) and the 5'-to-3' exonuclease activity of SURVEYOR Nuclease creates 3'-overhangs at both ends of the full-length molecules that will compete for capture with the specific 3'-overhangs of the digested fragments created from the internal cut at the mismatch.

To increase the specificity of capturing the 3'-overhang at the mismatch cut site, the digested fragments in the DNA population were specifically enriched after the SURVEYOR Nuclease digestion using Streptavidin magnetic beads. Introduction of biotin at the 5'-ends of a PCR fragment and subsequent binding to Streptavidin attached to beads protected the 5'-ends of the fragment from SURVEYOR 5'-to-3' exonuclease. Therefore, this method can be used to prevent capture of the ends of full-length molecules.

Given a method to protect PCR product ends and to produce only mismatch 3'-overhangs in SURVEYOR Nuclease-treated DNA, a method for capturing and amplifying those 3'-ends was developed.

Enrichment of SURVEYOR Nuclease Digestion Products Using Streptavidin Magnetic Beads. Two sets of identical 632-bp Control G and Control C DNA fragments were amplified with a mixture of four primers as described in Example 1. This produced an equal mixture of four different products for each template: molecules with biotin at both 5'-ends, with biotin at the 5'-end of the upper strand, with biotin at the 5'-end of the lower strand and molecules without biotin. Equal amounts of the two reactions were mixed, annealed and bound to Streptavidin magnetic beads. The resulting beads were washed to eliminate non-specific binding of DNA and treated with SURVEYOR Nuclease in the presence of ENHANCER S and 1.5 mM $MgCl_2$ or 10 mM $MgCl_2$. The digested products were then eluted from the beads to capture digestion fragment 3'-overhangs. It is important to realize that in this method only 50% of the molecules are heteroduplices and 50% of the heteroduplices are lost because they lack biotin and don't bind to Streptavidin or because they have biotin at both ends and don't get released from the Streptavidin magnetic beads after the digestion. Thus, a maximum of 25% of the molecules were available for mismatch detection. In addition, only one of the two cleavage fragments of a heteroduplex bound at one end to Streptavidin was released after digestion. However, using this approach all uncut molecules would either be eliminated in the flow-through during washes, or would remain bound to the Streptavidin magnetic beads after the digestion, and all products eluted after the SURVEYOR Nuclease digestion would have a 3'-overhang derived from a mismatch site.

The validity of the method was tested by comparing SURVEYOR Nuclease digestion of annealed Control G/C PCR products either directly or after binding to Streptavidin magnetic beads and analyzing the products in a 2% (w/v) agarose gel. As expected, two digested products of 415 bp and 217 bp corresponding to the cleavage fragments at both sides of the mismatch cut site were visualized in the gel in both samples. However, the results showed an almost complete (>100-fold) elimination of full-length PCR products and a similar enrichment of the digestion fragments when the annealed Control G/C PCR products were digested by SURVEYOR Nuclease after binding to Streptavidin magnetic beads.

RD-PCR. The capture of the 3'-ends of the cleavage fragments generated by SURVEYOR Nuclease digestion is required to provide the sequence identity of the mismatch. RD-PCR was used here to capture the 3' -overhangs produced by mismatch-specific endonucleases at a mismatch (FIG. 1). A linker containing a mixture of oligonucleotides with one, two or three protruding degenerate bases were ligated at the 3'-end (each position containing an equal mixture of A, T, C or G) to SURVEYOR Nuclease-digested DNA. One strand of linker subpopulations, carrying bases complementary to the 3'-overhangs created after the SURVEYOR Nuclease cut, was annealed to the overhangs. The phosphorylated, receding 5'-end of the complementary strand of the linker was then ligated to the 3'-overhangs of the digested PCR fragments at the mismatch. Formation of dimers between linkers was prevented by adding amino groups to the 3'-ends of both linker strands. The ligation products were then amplified by PCR using a primer complementary to the sequence of Control G/C PCR fragment and another complementary to the linker sequence.

To demonstrate the validity of the method, a Control G/C homoduplex/heteroduplex mixture was generated utilizing PCR products prepared as described in Example 1. The DNA mixture was digested with SURVEYOR Nuclease in the absence of Streptavidin beads and subjected to the RD-PCR procedure. Analysis of the PCR fragments generated after RD-PCR revealed minor amounts of a 450-bp fragment using pCEL190F30 (a specific primer that anneals to the 5'-end of the Control G/C PCR product) and M13uniPCR (a primer that anneals to the linker sequence) and minor amounts of a 250-bp fragment using pCEL81OR25 (a specific primer that anneals to the 3'-end of the Control G/C PCR product) and M13uniPCR. Since the size of the linker was 41-bp, the size of these fragments corresponded to the expected amplified fragment sizes upstream and downstream of the SURVEYOR Nuclease cut site. A major 650-bp product was also present in the RD-PCR amplification, produced by amplification of the 632-bp original full-length Control G/C. This was the result of SURVEYOR 5'-to-3' exonuclease activity creating 3'-overhangs at the ends of full-length Control G/C PCR product, allowing ligation of these ends to the linker. These results demonstrated that the RD-PCR linker was ligated successfully to all three types of exposed 3'-overhangs generated by SURVEYOR Nuclease in the absence of Streptavidin.

Enrichment of SURVEYOR Nuclease Digestion Products Using Streptavidin Magnetic Beads Reduces Amplification of Full-length Molecules after RD-PCR. A Control G/C homoduplex/heteroduplex mixture was again generated using PCR products prepared as described in Example 1. The mixture was bound to Streptavidin beads, the beads were washed, the bound DNA was digested with SURVEYOR Nuclease, and cleaved fragments were recovered from the supernatant and subjected to RD-RCR as described in Example 1. Agarose gel analysis of the fragments amplified by RD-PCR showed that binding annealed Control G/C PCR products to Streptavidin magnetic beads to elute only SURVEYOR Nuclease digested fragments prevented amplification of most of the full-length molecules. These results confirmed that this method substantially reduces the number of full-length molecules and enriches cleavage products present after RD-PCR.

DNA Sequence Analysis of Cleavage Fragments Captured by RD-PCR. PCR fragments released from Streptavidin magnetic beads after digestion with SURVEYOR Nuclease in the presence of 1.5 mM $MgCl_2$ and amplified by RD-PCR were cleaned up with a QIAGEN PCR Purification Kit according to the manufacturer's instructions, and were sequenced using a primer positioned at the upstream end of Control G/C PCR product. The amplified DNA was contaminated with a small amount of full-length Control G/C product. DNA sequencing through the 3'-end of the upstream cleavage fragment amplified by RD-PCR and into the linker sequence showed a clean chromatogram up to the mutation point. From this position and for approximately 45 bases, the chromatogram contained mixed sequences that corresponded to a mixture of the full-length Control G/C and linker sequences. After the 45 bases, the sequence was again clean and corresponded to the sequence of full-length Control G/C. It is contemplated that the mixed sequence observed across the linker region was a consequence of the presence of a mixed population of molecules produced by linker ligated to: 3'-overhangs created by SURVEYOR Nuclease cutting at the mismatch site and 3'-overhangs created by SURVEYOR Nuclease 5'-to-3' exonuclease activity nibbling at the ends of full-length Control G/C molecules. Thus, even though the application of the Streptavidin magnetic bead procedure prior to RD-PCR enriches cleavage fragments >100 fold over full-length fragments, some full-length DNA persists to create a secondary pattern during subsequent sequencing of the RD-PCR amplified DNA.

To confirm this, cleavage fragments of the appropriate size from Control G/C were eluted from Streptavidin magnetic beads, amplified by RD-PCR, and isolated from agarose gels to eliminate any contamination with full-length Control G/C. The fragments were sequenced using primers specific to the Control G/C PCR fragment. Sequencing chromatograms produced from these samples showed an abrupt end to the sequencing reaction 41 bases downstream from the mutation point, identical to the length of the linker, as would be expected if the end of the amplified fragment was encountered during sequencing. This result showed that indeed total elimination of full-length product results in removal of the secondary sequence from the chromatogram.

High $MgCl_2$ Concentrations Reduces SURVEYOR Nuclease 3'-to-5' Exonuclease Activity. SURVEYOR Nuclease digestions for the experiments just described were carried out in the presence of 1.5 mM $MgCl_2$ and 10 MM $MgCl_2$. Sequencing chromatograms of agarose gel-purified RD-PCR products derived from Control G/C digested in 10 mM $MgCl_2$ showed clean sequences after the mutation point and the sequence of the linker was picked up by standard sequencing programs. A careful analysis of the chromatograms showed almost negligible contamination and very sharp peaks. A high $Mg^{2+}$ concentration suppresses the 3'-to-5' exonuclease activity of SURVEYOR Nuclease sufficiently to produce amplified RD-PCR fragments that can be sequenced to yield readable chromatograms (FIGS. 5A and 5B).

SURVEYOR Nuclease Favors Digestion of C/C to G/G Mismatches in Control G/C. The sequencing chromatograms showed a mixture of C and G at the mutation point, as would be expected from SURVEYOR Nuclease cleavage of the G/G and C/C containing heteroduplices in Control G/C. However, the peak corresponding to C was higher than the peak corresponding to G (FIGS. 5A and 5B). These results are consistent with previous data using mismatched oligonucleotides substrates to establish mismatch cutting preferences of SURVEYOR Nuclease (Qiu, et al. (2004) supra) that indicated C/C is cut much more efficiently than G/G.

SURVEYOR Nuclease Produces an Asymmetric Cut at the Mismatch Site in Control G/C. When sequencing chromatograms from the RD-PCR fragment upstream of the mismatch site in Control G/C (450 bp) were compared with chromatograms from the fragment downstream of the mismatch (250 bp), an unexpected result was observed (FIGS. 5A and 5B). For the downstream 250-bp fragment, the sequence clearly showed that the 5'-end of the linker was ligated to the 3' G or C overhang at the mutation site. In contrast, a T was observed in the upstream 450-bp fragment between the 3'-end of the mutation and the 5'-end of the linker. In Control G/C DNA, there was a T adjacent and 3' to the mismatch C/G site. These results are consistent with SURVEYOR Nuclease cutting the Control C/C heteroduplex 3' to the T adjacent and 3' to the C/C mismatch, producing a two-base CT 3'-overhang in one strand and a single base C 3'-overhang in the other strand.

Based upon the analysis conducted herein, particular embodiments of the present invention provide for the use of high concentrations of $Mg^{2+}$ (in the range of 1.5 to 20 mM) when employing SURVEYOR Nuclease to efficiently capture the 3'-overhang at an endonuclease mismatch cut site.

Example 3

Libraries of Genomic DNA with Genetic Variations

A specific protocol for generating libraries of genomic DNA with genetic variations, designated herein as SNAIL (SURVEYOR Nuclease Adaptor Integration Libraries), is described below. By way of illustration the above protocol is carried out with known amounts of a heterozygous segment of human DNA spiked into *E. coli* genomic DNA. The SNAIL methodology is used to generate SNAIL libraries in *E. coli* cells by inserting the DNA fragments from the SNAIL process into a vector, transforming *E. coli* cells with the recombinants, and sequencing the DNA from individual colonies by classical Sanger cycle sequencing. The *E. coli* genomic DNA is derived from two *E. coli* K-12 genomes that are cross-hybridized, one is wild-type and the other has been mutagenized by treatment with MNNG to contain one mutation every 12,000 bases, thus creating a mutant background for the spiked human DNA.

Materials. SURVEYOR Nuclease (CEL II) was purified from celery by a modification of known methods (Yang, et al. (2000) supra; Gerard, et al. (2006) supra). Enzymatic activity was assigned based upon a denatured DNA solubilization assay performed at pH 8.5 (Yang, et al. (2000) supra). One unit of solubilization activity was defined as the amount of enzyme required to produce 1 ng of acid-soluble material in 1 minute at 37° C. OPTIMASE and MAXIMASE™ Polymerase were from Transgenomic, Inc (Omaha, Nebr.).

M-280 Streptavidin magnetic DYNABEADS® were from Dynal Biotech (INVITROGEN, Carlsbad, Calif.). Nebulizers were purchased from Invitrogen (Carlsbad, Calif.). Cloned Taq DNA ligase was prepared by Transgenomic, Inc. Streptavidin was purchased from SIGMA (Sigma/Aldrich, St. Louis, Mo.). T4 DNA polymerase, T4 polynucleotide Kinase, T4 DNA ligase, Klenow Fragment DNA polymerase, EcoRI restriction enzyme, NotI restriction enzyme, and *E. coli* DNA polymerase I were purchased from New England BioLabs (Ipswich, Mass.). Exonuclease V was purchased from USB (Cleveland, Ohio).

Oligonucleotides. Oligonucleotides were synthesized by Sigma-Genosys (The Woodlands, Tex.). Unless indicated otherwise, oligonucleotides were desalted before use. The oligonucleotides included:

BioEco Adaptor Up (PAGE purified); upper strand of the Double-Stranded Adaptor that is biotinylated at the 5' end: 5'-Biotin-CAC ACA TCC ATC ATC ATC ATG AAT TCC AGA CAT CAG GCA GGC ATC AGA (SEQ ID NO:14); BioEco Adaptor Low; lower strand of the Double-Stranded Adaptor with a blocking amino group at the 3' end: TCT GAT GCC TGC CTG ATG TCT GGA ATT CAT GAT GAT GAT GGA TGT GTG-$NH_4^+$-3' (SEQ ID NO:15); M13 RDPCR Top (gel purified); upper strand of the Double-Stranded Linker with a phosphate at the 5' end and a blocking amino group at the 3' end: 5'-$PO_4$-CGA CTG GAG CAC GAG GAC ACT ACT GGC CGA CGT TTT ACA CC—$NH_4^+$-3' (SEQ ID NO:16); M13 RDPCR Bottom 5' Biotin (gel purified); 5' portion of the lower strand of the Double-Stranded Linker with a biotin at the 5' end: 5'-Biotin-GGT GTA AAA CGT CGG CCA GTA GTG TCC TC (SEQ ID NO:17); and M13-NN-bottom 3' PO4 14bp; 3' portion of the lower strand of the Double-Stranded Linker with two degenerate bases and a blocking phosphate at the 3' end: 5'-GTG CTC CAG TCG NN—$PO_4$-3' (SEQ ID NO:18). A double degenerate linker was used in this protocol.

Amplification of Target Mutant Human DNA. Wild-type DNA and a single point mutant DNA in exon 24 of the human ABCC6 gene that causes PXE were PCR amplified, the PCR products were purified and quantified. Annealing the PCR products produced human DNA with a single mismatch site.

The wild-type and mutant DNA segments were carried on plasmids designated pPxeExon24wt and pPxeExon24mut4, respectively. The PCR primers used to amplify PXE exon 24 were Pxe24PO4For (PAGE purified; 10 μM): $PO_4$-GCA AGG AAA TGA GAA CCC AGA GAG GGC AAG (SEQ ID NO:19) and Pxe24PO4Rev (PAGE purified; 10 μM): $PO_4$-GAT AGA CTG CCT GTG GGA TCT AGC CTC (SEQ ID NO:20). Amplification reaction mixtures (50 μL) contained template DNA (1 μL, 10 ng), 1 μL of 10 μM Forward Primer, 1 μL of 10 μM Reverse Primer, 1 μL of 10 mM dNTPs, 5 μL of 10× OPTIMASE Buffer (100 mM Tris-HCl, pH 8, 750 mM KCl, 15 mM $MgSO_4$, 0.1% (v/v) TRITON-X 100), 0.5 μL of 6 units/μL OPTIMASE polymerase and 40.5 μL of $H_2O$. PCR was performed with the following program: 94° C., 2 minutes; 24 cycles of 94° C., 30 seconds, 64° C., 30 seconds, and 72° C., 1 minute; 72° C., 5 minutes; and 4° C., hold. PCR amplified DNA was purified using a QIAGEN PCR Purification Kit according to the manufacturer's instructions and the DNA concentration was determined using a Nanodrop Spectrophotometer.

The steps for generating a SNAIL library in *E. coli* cells were performed in accordance with the method of the invention as follows.

(a) Nebulize Genomic DNA. Wild-type and mutant *E. coli* genomic DNA (10 μg) were each placed separately in 750 μL of Nebulizer Buffer (10 mM Tris-HCl (pH 8.0), 1 mM EDTA, 10% (v/v) glycerol) at 4° C. The solution was placed in a nebulizer chamber on ice and subjected to a pressure of 15 psi for 60 seconds. This produced a DNA population with a size range of 600 to 2,200 bp centered around 1,200 bp.

In preparation for Step (b), the DNA was concentrated by addition of sodium acetate to 0.3 M, glycogen to 0.1 μg/μL, and 2.5 volumes of ethanol followed by centrifugation. The pellet was washed with 80% (v/v) ethanol and the DNA was dissolved in T0.1E (10 mM Tris-HCl, pH 8.0, 0.1 mM EDTA) to a concentration of >0.5 μg/μL. Concentration was determined by reading the absorbance at 260 nm.

(b) Heat and Anneal Genomic DNA. The DNA was annealed in a thermocycler in a 0.2-mL tube in a 30-μL volume containing 5 μL of wild-type and 5 μL of mutant *E. coli* DNA at 0.5 μg/μL, various amounts of wild-type and mutant PXE PCR product, 1.5 μL 1 M HEPES (pH 7.5), 3 μL 5 M NaCl, and $H_2O$ to a final volume of 30 μL. The annealing program was 94° C., 4 minutes; 68° C., 72 hours; and −0.1° C./second to 25° C.

The DNA was ethanol precipitated by addition of 2.5 volumes of ethanol and centrifugation and dissolved in a minimum volume (~50 μL) of T0.1E in preparation for repair of DNA ends (step c). The concentration was determined by measuring the absorbance at 260 nm.

(c) Treat the Genomic DNA with T4 DNA Polymerase, Klenow Fragment DNA Polymerase, dNTPs, T4 Polynucleotide Kinase, and ATP and Clean Up the DNA to Remove Enzymes and Cofactors. The ends of the annealed DNA were repaired in a 50-μL reaction mixture set up at room temperature by adding constituents in the following order: 23.4 μL $H_2O$, 5 μL 1× NEBuffer 2, 2.5 μL 10 mM dNTPs (GE Healthcare), 5 μL 10 mM ATP (GE Healthcare), 0.5 μL 10 mg/mL BSA (NEB), 1 μL 0.1 M DTT, 1 μL 10 units/μL T4 polynucleotide Kinase, 1 μL 3 units/μL T4 DNA polymerase, 0.6 μL 5 units/μL Klenow Fragment DNA Polymerase, and 10 μL 100 ng/μL annealed DNA. The mixture was incubated at room temperature for 45 minutes. EDTA (5 μL of 0.5 M) was added and the mixture was heated at 70° C. for 20 minutes.

The DNA was ethanol precipitated in preparation for step (d) by the addition of 1.5 μL of QUICKPRECIP (Edge BioSystems), 6 μL of 5 M NaCl, and 180 μL of ethanol followed by centrifugation. The pellet was washed with 80% (v/v) ethanol and dissolved in 10 μL of T0.1E.

(d) Using T4 DNA Ligase, Ligate the Double-Stranded Adaptor Which Contains a Restriction Enzyme Cut Site and a Biotin Molecule at One 5' End to the Ends of the Repaired DNA. The Double-Stranded Adaptor has an EcoRI cut site 21 nucleotides from the 5' end, a biotin at the 5' end of the upper strand, and a amino blocking group at the 3' end of the lower strand (see Oligonucleotide Section). The upper and lower strands of the Double-Stranded Adaptor were annealed in a thermocycler in a 0.2-mL tube in equal molar amounts in 1× Annealing Buffer (10 mM Tris-HCl, pH 8.0, and 50 mM NaCl) at a final concentration of 0.9 μg/μL each. The annealing program was:

| | |
|---|---|
| 95° C. | 10 minutes |
| 95° C. to 85° C. | (−2.0° C./s) |
| 85° C. | 1 minute |
| 85° C. to 75° C. | (−0.3° C./s) |
| 75° C. | 1 minute |
| 75° C. to 65° C. | (−0.3° C./s) |
| 65° C. | 1 minute |
| 65° C. to 55° C. | (−0.3° C./s) |
| 55° C. | 1 minute |
| 55° C. to 45° C. | (−0.3° C./3) |
| 45° C. | 1 minute |
| 45° C. to 35° C. | (−0.3° C./s) |
| 35° C. | 1 minute |
| 35° C. to 25° C. | (−0.3° C./s) |
| 25° C. | 1 minute |
| 4° C. | Hold. |

Double-Stranded Adaptor (3 μL; 2.7 μg), repaired DNA (10 μL; ~1 μg), 2× PEG Ligation Buffer (13 μL; 132 mM Tris-HCl, pH 7.6, 20 mM $MgCl_2$, 2 mM DTT, 2 mM ATP, 15% (w/v) PEG 6000), and High Concentrate T4 DNA ligase (1 μL; 2,000 units/μL) were mixed and incubated at 16° C. for 1 hour followed by 65° C. for 10 minutes. Approximately 80% of the DNA had adaptor ligated at both ends.

(e) Size Fractionate DNA with SEPHACRYL S-400 HR to Remove Excess Double-Stranded Adaptors and Repair the Nick in the Double-Stranded Adaptors at the Ends of the DNA with *E. coli* DNA polymerase I. The procedure for size fractionation is described below, wherein the ligation product was size fractionated to remove excess Double-Stranded Adaptors and any small DNA fragments (<100 bp).

Column Packing. Columns were packed individually by gravity according to the following method. The final packed resin bed was 0.7×5 cm (d×h).

1. Cap the bottom of the column.
2. Fill the column with Fractionation Buffer (10 mM Tris-HCl, pH 8.0, 150 mM NaCl, 0.1 mM EDTA).
3. Wet a frit with the buffer inside the column and push the frit to the column bottom as far as it can go with the top, back of a Pasteur pipette.
4. Open and close the bottom cap of the column to eliminate air, bringing the liquid level to 0.5 cm below the top.
5. Open the bottom of the column and pipette 4 mL of a 50% slurry of SEPHACRYL S-400 that has been equilibrated and washed in Fractionation Buffer.
6. Let the resin settle, fill reservoir with buffer, and wet another frit.
7. Push the frit down towards the resin bed as before leaving about 0.5 mm between top of the resin bed and bottom of the frit.
8. Remove the buffer from the column reservoir to eliminate residual resin and refill the reservoir with buffer.
9. Drain the buffer, fill the reservoir again with buffer and put the top lid and bottom cap on the column.

Running the Column. Columns were run by gravity in Fractionation Buffer.

1. Remove the top lid and bottom cap and let the buffer drain to the top frit.
2. Apply the ligation mix from step d (about 25 μL) and let it drain. Discard the eluant.
3. Apply 25 μL of Fractionation Buffer and let it drain. Discard the eluant.

4. Apply 850 μL of Fractionation Buffer and let it drain. Collect the eluant in one fraction in case the column is not running properly. This fraction should not have any DNA.
5. Apply 300 μL of Fractionation Buffer and collect the eluant in one fraction.
6. Fill reservoir with Fractionation Buffer and drain the column.
7. Fill reservoir with Fractionation Buffer and put top lid and bottom cap on the column for storage.

DNA Precipitation. DNA in the second column fraction was ethanol precipitated by mixing 300 μL DNA, 2.5 μL QUICKPRECIP, 35 μL 5 M NaCl, and 1 mL absolute ethanol at room temperature and centrifuging. The pellet was washed with 80% (v/v) ethanol and dissolved in 15 μL of T0.1E. The DNA concentration was determined using a Nanodrop Spectrophotometer. The recovery was ~0.6 μg of DNA.

Procedure for DNA End Repair. Because the Double-Stranded Adpators ligated to the DNA in step (d) lacked phosphate groups (to prevent dimerization of adaptor), a nick was present near the 3' end of each strand of the DNA. The nick was removed by nick-translation DNA synthesis with *E. coli* DNA polymerase I. The reaction mixture was set up on ice by adding the following components to a 30-μL reaction in the order shown: 10.25 μL $H_2O$, 3 μL 10× Pol I Reaction Buffer (100 mM Tris-HCl, pH 7.25, 500 mM KCl, 100 mM $MgCl_2$, 10 mM DTT, and 1000 μg/mL BSA), 0.75 μL 10 mM dNTPs, 15 μL DNA (~600 ng), and 1 μL 10 units/μL DNA polymerase I. The reaction was incubated at 16° C. for 60 min. After adding 3 μL of 0.5 M EDTA, the mixture was heated at 70° C. for 20 minutes. The DNA was ethanol precipitated and the pellet dissolved in 30 μL of T0.1E in preparation for step (f).

(f) Bind Linear Genomic DNA to Streptavidin Beads and Wash. The DNA from step (e) was bound to Streptavidin (SA) beads using the biotin moiety at the 5' end of the Double-Stranded Adaptors ligated to the ends of the DNA in step (d).

Washing SA Beads. For 600 ng of DNA, 30 μL of SA bead slurry at 10 mg/mL was used. The beads were placed in a 1.5-mL snap cap tube and 30 μL of 2× B/W Buffer (20 mM Tris-HCl, pH 8.0, 2 M NaCl, 1 mM EDTA) was added and mixed. The supernatant was removed using a magnet and the washing step was repeated 2 more times. The beads were suspended in 30 μμL of 2× B/W Buffer.

Binding DNA to Washed Beads. In a 0.2-mL tube of a PCR strip (at least 3 tubes should be present in the strip to facilitate manipulation), 30 μL of washed beads in 2× B/W Buffer were mixed with 30 μL of the DNA from step (e). The suspension was incubated at room temperature for at least 20 minutes using a rotary device to keep the beads suspended. The tube strip was inserted in a magnet and the supernatant was recovered and placed in a separate tube. The beads were suspended in 30 μL of 1× B/W Buffer in preparation for step (g). The amount of DNA in the supernatant was quantified by determining the $A_{260}$. Around 90% of the DNA bound to the beads.

(g) Treat the Bound DNA with Exonuclease V to Degrade DNA Not Bound to Beads and Wash the Beads to Remove Exonuclease. The 30 μL of beads (0.3 mg) from step (f) were washed 3 times with 200 μL of 1× Exo V Reaction Buffer (66.7 mM Glycine-KOH, pH 9.4, 30 mM $MgCl_2$, 8.3 mM β-Mercaptoethanol,0.5 mM ATP, and 100 μg/mL BSA) and adjusted to a concentration of 5 mg beads/mL in 60 μL of 1× Exo V Reaction Buffer. A 120-μL reaction mixture was set up on ice by mixing the following components in the order shown: 53.4 μL $H_2O$, 6 μL 10× Exo V Reaction Buffer, 60 μL beads, and 0.6 μL 10 units/μL Exonuclease V. After a 30 minute incubation at 37° C., the beads were washed 3 times with 200 μL of 1× Exonuclease V Reaction Buffer, 3 times with 1× B/W buffer, and 3 times with 1× SURVEYOR Nuclease Reaction Buffer (20 mM Tris-HCl, pH 9.0, 50 mM KCl, and 10 mM $MgCl_2$) and suspended in 30 μL of the same buffer for step (h).

(h) Treat Sample with SURVEYOR Nuclease, Taq DNA Ligase and NAD and Wash the Beads to Remove Enzymes and Cofactors. The DNA bound to SA beads was digested with SURVEYOR Nuclease in the presence of high $Mg^{++}$ and Taq DNA ligase to suppress matched site nicking. A 60-μL reaction mixture was set up by mixing the following components in the order shown: 15 μL $H_2O$, 3 μL 10× SURVEYOR Nuclease Reaction Buffer, 30 μL Streptavidin beads, 6 μL 10 mM β-AND, 3 μL 120 units/μL Taq DNA ligase, and 3 μL 10 units/μL SURVEYOR Nuclease. After a 20-minute incubation at 42° C., 6 μL of 0.5 M EDTA were added. The beads were washed 5× with 120 μL of 1× B/W Buffer in preparation for step (i) and suspended in 30 μL of 1× B/W Buffer.

(i) Treat Beads with Excess Biotin to Occupy all Streptavidin Sites and Wash the Beads. Free biotin was added to the Streptavidin beads with bound DNA from step (h) to block all reactive Streptavidin moieties on the beads. A 20-fold molar excess of free biotin was used.

The 1× B/W buffer was removed from beads from step (h) using a magnet and 30 μL of a 140 μM biotin solution was added. The beads were pipetted up and down to mix and the suspension was incubated at room temperature for at least 20 minutes using a rotary device to keep the beads suspended. The beads were washed 5 times with 120 μL of 1× B/W Buffer as described in step (f). The beads were suspended in 30 μL of 1× B/W Buffer in preparation for step (j).

(j) Using T4 DNA Ligase, Ligate the Double-Stranded Linker to the Genomic DNA and Wash.

Annealing Adaptor Oligonucleotides. Dried oligonucleotides were dissolved in T0.1E at 1.5 μg/μL and the concentration determined by reading the absorbance at 260 nm. The three oligonucleotides (M13 RDPCR Top; M13 RDPCR Bottom 5' Biotin; M13-NN-bottom3' PO4 14-bp) were annealed in a thermocycler in a 0.2-mL tube in equal molar amounts in 1× Annealing Buffer at a final concentration of 1 μg/μL each. The annealing program was:

| | |
|---|---|
| 95° C. | 10 minutes |
| 95° C. to 85° C. | (−2.0° C./s) |
| 85° C. | 1 minute |
| 85° C. to 75° C. | (−0.3° C./s) |
| 75° C. | 1 minute |
| 75° C. to 65° C. | (−0.3° C./s) |
| 65° C. | 1 minute |
| 65° C. to 55° C. | (−0.3° C./s) |
| 55° C. | 1 minute |
| 55° C. to 45° C. | (−0.3° C./s) |
| 45° C. | 1 minute |
| 45° C. to 35° C. | (−0.3° C./s) |
| 35° C. | 1 minute |
| 35° C. to 25° C. | (−0.3° C./s) |
| 25° C. | 1 minute |
| 4° C. | Hold. |

Ligation of Double-Stranded Linker to SA bead-bound DNA. The bead suspension from step (i) (30 μL) was mixed with 2× PEG Ligation Buffer (36 μL), Double-Stranded Linker (0.45 μL; 0.45 μg), and High Concentrate T4 DNA ligase (3 μL; 2,000 units/μL) and incubated at 16° C. for 1 hour. The beads were washed 3 times with 120 μL of 1× B/W buffer as described in step (f) and suspended in 30 μL of 1× B/W buffer in preparation for step (k).

The efficiency of ligation was approximately 50%.

(k) Treat the Bound DNA with *E. coli* DNA Polymerase I (Pol I) and dNTPs and Wash to Remove the Enzyme and Cofactors. The nick in the bottom strand of the Double-Stranded Linker ligated to the SURVEYOR Nuclease cleaved ends is removed by nick translation with Pol I.

The beads from step (j) were washed 3 times with 1× Pol I Reaction Buffer and adjusted to a concentration of 10 mg/mL (30 μL). The following 60-μL reaction mixture was set up on ice adding the components in the order shown: 24 μL $H_2O$, 3 μL 10× PolI Reaction Buffer, 1.5 μL 10 mM dNTPs, 30 μL beads in 1× PolI Reaction Buffer, and 1.5 μL 10 units/μL Pol I. After incubating for 2 hours at 16° C., 6 μL of 0.5 M EDTA were added. The beads were washed 3 times with 1× EcoRI Reaction Buffer (100 mM Tris-HCl, pH 7.5, 50 mM NaCl, 10 mM $MgCl_2$, 0.025% (v/v) TRITON X-100) and suspended in 30 μL of 1× EcoRI Reaction Buffer.

(l) Release the DNA from the SA Beads by Treatment with EcoRI. The DNA bead suspension from step (k) (30 μL) was mixed with 6 μL of $H_2O$, 1 μL of 10× EcoRI buffer and 3 μL of 20 units/μL EcoRI. After a 60-minute incubation at 37° C. the enzyme was inactivated by heating at 65° C. for 20 minutes. The supernatant was recovered using a magnet. The beads were washed once with 1× B/W buffer (20 μL) and the wash was combined with the supernatant.

This step releases 50-60% of the DNA from the beads.

(m) Bind the Genomic DNA to Fresh SA Beads Through the Biotin at the End of the Double-stranded Linker Ligated to the DNA. SA beads (20 μL; 10 mg/mL) were washed 3 times with 2× B/W buffer and the beads were suspended in 20 μL of 2× B/W Buffer. In a 0.2-mL tube of a PCR strip (at least 3 tubes should be present in the strip to facilitate manipulation), 20 μL of washed beads in 2× B/W Buffer were mixed with 40 μL 2× B/W Buffer and 60 μL of DNA from step (l). The suspension was mixed at room temperature for at least 20 minutes using a rotary device to keep the beads suspended. The tube strip was inserted in a magnet, the supernatant was recovered and placed in a separate tube, and the beads were suspended in 30 μL of 1× B/W Buffer in preparation for step (n).

(n) Elute the Non-biotinylated DNA Strand from the SA beads by Alkaline Treatment. One strand of the double-stranded DNA bound to the SA beads was not covalently bound to biotin and thus could be removed from the SA beads by alkaline denaturation for further manipulation.

To dissociate DNA strands from beads, the 1× B/W Buffer was removed from the beads from step m using a magnet. Alkaline Elution Solution (5 μL; 125 mM NaOH and 100 mM NaCl) was added to the beads and the suspension was incubated at room temperature for 10 minutes. Using a magnet, the supernatant was removed and placed in a separate tube and neutralized by the addition of 4.5 μL of Acid-Tris Solution (10 mM Tris-HCl, pH 7.5 and 125 mM HCl).

(o) PCR Amplify the Single-Stranded DNA. The single-stranded DNA from step (n) was made double-stranded by performing a minimum number of PCR cycles using Maximase DNA polymerase. By use of appropriate sequences at the 5'-ends of PCR primers, ends were introduced into the double-stranded DNA that were compatible with cloning into the vector used in the next step. The primers used were 5CR4.infus.F (10 μM) 5'-GGT TTA AAC GAA TTC CAG ACA TCA GGC AGG CAT CAG A-3' (SEQ ID NO:21) and 3UCR4.R (10 μM) 5'-ttg aat tta gcg gcc GGT GTA AAA CGT CGG CCA GTA GTG-3' (SEQ ID NO:22).

The following reaction mixture was prepared on ice by addition of the components listed to a 0.2-mL tube: 2 μL $H_2O$, 9.5 μL neutralized DNA, 1.5 μL 10× MAXIMASE Reaction Buffer (with 20 mM $MgSO_4$), 0.5 μL 10 mM dNTPs, 0.5 μL 10 μM 5CR4.infus.F, 0.5 μL 10 μM 3UCR4.R, and 0.5 μL 5 units/μL MAXIMASE DNA polymerase. PCR was carried out as follows: 95° C./2 minutes; 5 cycles of 95° C./30 seconds, 55° C./30 seconds, and 72° C./1 minute; 72° C./10 minutes; and 4 ° C./hold. The DNA was then ready for cloning into vector in step (p).

(p) Insert the Amplified DNA into Vector and Transform *E. coli* Cells. An *E. coli* library was prepared from the amplified DNA using the IN-FUSION™ 2.0 Dry-Down PCR Cloning Kit (Clontech). To prepare the vector DNA, 5 μg of pCR4 vector plasmid DNA was cut with 20 units of NotI restriction enzyme in 100 μL 1× NEB EcoRI Buffer at 37° C. for one hour and then with 20 units of EcoRI restriction enzyme at 37° C. for an additional hour. The linearized vector DNA was isolated on a 1% (w/v) agarose gel and purified with a QIAQUICK Gel Extraction Kit (QIAGEN).

The IN-FUSION cloning was carried out as per the manufacturer's instructions. To perform IN-FUSION cloning, 5 μL of the PCR product was mixed with 2 μL IN-FUSION ENHANCER, and the mixture was incubated at 37° C. for 15 minutes and then at 80° C. for 15 minutes.

IN-FUSION ENHANCER-treated insert (7 μL) was mixed with 100 ng linearized vector DNA in a 10 μL volume. The IN-FUSION reaction was carried out by placing the insert-vector mixture in an IN-FUSION dry-down reaction tube and incubating at 37° C. for 15 minutes and then at 50° C. for 15 minutes. TE buffer (40 μL) was added at the end of the reaction.

Transformation of *E. coli* competent cells supplied in the IN-FUSION Kit was carried out with 2.5 μL of treated DNA.

What is claimed is:

1. A method for producing a library of genomic DNA molecules containing genetic variations comprising (a) fragmenting one or more samples of genomic DNA;

(b) denaturing and annealing the fragmented genomic DNA to generate double-stranded genomic DNA molecules, wherein one strand of said double-stranded genomic DNA molecules has one or more variant nucleotides which create at least one mismatch in the double-stranded genomic DNA molecules;

(c) blunt ending, dephosphorylating 3' ends, and phosphorylating 5' ends of the double-stranded genomic DNA molecules;

(d) ligating a Double-Stranded Adaptor onto ends of the double-stranded genomic DNA molecules, wherein said Double-Stranded Adaptor contains a restriction enzyme cut site and a functional group at one 5' end;

(e) size fractionating the double-stranded genomic DNA molecules of step (d) to remove the Double-Stranded Adaptor;

(f) immobilizing the size fractionated, double-stranded genomic DNA molecules via binding of the functional group of the Double-Stranded Adaptor to reactive groups of a first solid support;

(g) removing double-stranded genomic DNA molecules which are not immobilized by the first solid support;

(h) contacting the immobilized double-stranded genomic DNA molecules with a mismatch-specific endonuclease so that the double-stranded genomic DNA molecules are cleaved at the 3'-side of the mismatches therein;

(i) ligating a Double-Stranded Linker to the 3'-end of the immobilized genomic DNA molecules, wherein one strand of the Double-Stranded Linker contains a nick, a functional group at the 5' end and a degenerate sequence at the 3' end, wherein the degenerate sequence is a 3'-overhang, and the double-stranded portion of the linker is of a predetermined sequence;

(j) repairing nicked DNA of the product of step (i);

(k) immobilizing the Double-Stranded Linker ligated to the immobilized double-stranded genomic DNA molecules via binding of the functional group of the Double-Stranded Linker to reactive groups of a second solid support; and (l) contacting the product of step (k) with a restriction enzyme which cleaves the Double-Stranded Adaptor at the restriction enzyme cut site thereby releasing the double-stranded genomic DNA molecules from the first solid support thereby creating a library of genomic DNA molecules containing genetic variations.

2. The method of claim 1, wherein steps (h) through (k) are repeated one or more times.

3. A method for identifying the sequence of one or more variant nucleotides in a nucleic acid molecule comprising (a) contacting a double-stranded nucleic acid molecule with a mismatch-specific endonuclease, wherein one strand of said double-stranded nucleic acid molecule has one or more variant nucleotides which create at least one mismatch in the double-stranded nucleic acid molecule so that the double-stranded nucleic acid molecule is cleaved at the 3'-side of the mismatch by the mismatch-specific endonuclease, wherein the double-stranded nucleic acid molecule is double-stranded genomic DNA produced by:

(i) fragmenting one or more samples of genomic DNA;

(ii) denaturing and annealing the fragmented genomic DNA to generate double-stranded genomic DNA molecules, wherein one strand of said double-stranded genomic DNA molecules has one or more variant nucleotides which create at least one mismatch in the double-stranded genomic DNA molecules;

(iii) blunt ending, dephosphorylating 3' ends, and phosphorylating 5' ends of the double-stranded genomic DNA molecules;

(iv) ligating a Double-Stranded Adaptor onto ends of the double-stranded genomic DNA molecules, wherein said Double-Stranded Adaptor contains a restriction enzyme cut site and a functional group at one 5' end;

(v) size fractionating the double-stranded genomic DNA molecules of step (iv) to remove the Double-Stranded Adaptor;

(vi) immobilizing the size fractionated, double-stranded genomic DNA molecules via binding of the functional group of the Double-Stranded Adaptor to reactive groups of a first solid support; and (vii) removing double-stranded genomic DNA molecules which are not immobilized by the first solid support;

(b) ligating a Double-Stranded Linker, containing a 3'-overhang, to the 3'-end of the strand with the one or more variant nucleotides, wherein the 3'-overhang of the linker is degenerate and the double-stranded portion of the linker is of a predetermined sequence; and (c) determining the sequence of the one or more variant nucleotides via the predetermined linker sequence thereby identifying the sequence of the one or more variant nucleotides.

4. The method of claim 3, wherein the 5'-end of at least one strand of the double-stranded nucleic acid molecule in step (a) is bound to a solid support.

5. The method of claim 3, wherein the 3'-ends of the double-stranded nucleic acid molecule in (a) are blocked.

6. The method of claim 3, wherein the strand with the one or more variant nucleotides is labeled.

7. The method of claim 3, wherein step (c) is carried out by sequencing-by-synthesis from the predetermined linker sequence.

8. The method of claim 3, wherein step (c) is carried out by (i) denaturing the double-stranded portion of the linker;

(ii) hybridizing a complementary primer to the predetermined linker sequence in the presence of an intercalating fluorescence resonance energy transfer (FRET) donor;

(iii) contacting the product of step (ii) with DNA Polymerase and at least one ddNTP labeled with a FRET acceptor to extend the complementary primer; and (iv) detecting FRET, wherein the presence of FRET is indicative of the sequence of the variant nucleotide.

9. The method of claim 3, wherein the Double-Stranded Linker is detectably labeled.

10. The method of claim 3, wherein the double-stranded nucleic acid molecule of step (a) is produced by a polymerase chain reaction.

11. The method of claim 10, wherein the polymerase chain reaction is carried out with a universal primer.

12. The method of claim 11, wherein the 5'-end of the universal primer is bound to a solid support.

13. The method of claim 3, wherein the Double-Stranded Linker further comprises a nick and a functional group at the 5' end of the strand containing the degenerate sequence and step (b) includes:

(i) immobilizing the Double-Stranded Linker ligated to the immobilized double-stranded genomic DNA molecules via binding of the functional group of the Double-Stranded Linker to reactive groups of a second solid support; and (ii) contacting the double-stranded genomic DNA molecules immobilized on the first solid support and second solid support with a restriction enzyme which cleaves the Double-Stranded Adaptor at the restriction enzyme cut site thereby releasing the double-stranded genomic DNA molecules from the first solid support.

14. A kit for identifying the sequence of one or more variants in a nucleic acid molecule comprising a mismatch-specific endonuclease that cleaves a double stranded nucleic acid molecule at the 3'-side of a mismatch;

a Double-Stranded Linker, containing a 3'-overhang, wherein the 3'-overhang of the linker is degenerate and the double-stranded portion of the linker is of a predetermined sequence; and a Double-Stranded Adaptor containing a restriction enzyme cut site and a functional group at one 5' end.

15. The kit of claim 14, further comprising a primer complementary to the predetermined sequence of the linker;

an intercalating FRET donor; and ddCTP, ddATP, ddTTP, and ddGTP each labeled with a different FRET acceptor.

* * * * *